(12) United States Patent
Webber et al.

(10) Patent No.: US 7,110,807 B2
(45) Date of Patent: Sep. 19, 2006

(54) METHOD AND SYSTEM FOR CREATING THREE-DIMENSIONAL IMAGES USING TOMOSYNTHETIC COMPUTED TOMOGRAPHY

(75) Inventors: Richard L. Webber, Winson-Salem, NC (US); Roger A. Horton, Winston-Salem, NC (US)

(73) Assignee: Wake Forest University Health Sciences, Winston-Salem, NC (US)

( * ) Notice: Subject to any disclaimer, the term of this patent is extended or adjusted under 35 U.S.C. 154(b) by 35 days.

(21) Appl. No.: 10/972,887

(22) Filed: Oct. 25, 2004

(65) Prior Publication Data

US 2005/0113682 A1    May 26, 2005

Related U.S. Application Data

(63) Continuation of application No. 09/862,006, filed on May 21, 2001, now Pat. No. 6,810,278, which is a continuation of application No. 09/034,922, filed on Mar. 5, 1998, now Pat. No. 6,289,235.

(51) Int. Cl.
*A61B 6/03* (2006.01)
(52) U.S. Cl. ..................... 600/426; 600/425
(58) Field of Classification Search ............ 600/414, 600/425, 426; 382/131, 294, 295
See application file for complete search history.

(56) References Cited

U.S. PATENT DOCUMENTS

| | | | |
|---|---|---|---|
| 4,662,379 A | 5/1987 | Macovski | |
| 4,722,056 A | 1/1988 | Roberts et al. | |
| 4,920,491 A | 4/1990 | Eberhard et al. | |
| 4,941,164 A | 7/1990 | Schuller | |
| 5,008,947 A | 4/1991 | Yamada | |
| 5,051,904 A | 9/1991 | Griffith | |
| 5,070,454 A | 12/1991 | Griffith | |
| 5,081,577 A | 1/1992 | Hatle | |
| 5,227,969 A | 7/1993 | Waggener et al. | |
| 5,299,254 A | 3/1994 | Dancer et al. | |
| 5,319,550 A | 6/1994 | Griffith | |
| 5,359,637 A | 10/1994 | Webber | |
| 5,642,293 A | 6/1997 | Manthey et al. | |
| 5,668,844 A | 9/1997 | Webber | |
| 5,694,530 A * | 12/1997 | Goto ........................ 345/419 |
| 5,751,787 A | 5/1998 | Jing et al. | |
| 5,755,725 A | 5/1998 | Druais | |
| 5,828,722 A | 10/1998 | Ploetz et al. | |
| 5,872,828 A | 2/1999 | Niklason | |
| 5,878,104 A | 3/1999 | Ploetz | |

(Continued)

FOREIGN PATENT DOCUMENTS

AU    697905    11/1993

(Continued)

OTHER PUBLICATIONS

EVS-125 X-Ray Slicer Catalog, Yunihaito Co., Ltd., Shinjuku-KU, Tokyo.

(Continued)

*Primary Examiner*—Brian L. Casler
*Assistant Examiner*—Julianne M. Sullivan
(74) *Attorney, Agent, or Firm*—Dann Dorfman Herrell and Skillman, P.C.

(57) ABSTRACT

A system for constructing image slices through a selected object, the system comprising an identifiable fiducial reference in a fixed position relative to the selected object, wherein the fiducial reference comprises at least two identifiable reference markers. A source of radiation is provided for irradiating the selected object and the fiducial reference to form a projected image of the selected object and the fiducial reference which is recorded by a recording medium.

41 Claims, 27 Drawing Sheets

U.S. PATENT DOCUMENTS

| | | |
|---|---|---|
| 6,081,577 A | 6/2000 | Webber |
| 6,118,845 A | 9/2000 | Simon et al. |
| 6,120,180 A | 9/2000 | Graumann |
| 6,122,541 A | 9/2000 | Cosman et al. |
| 6,249,568 B1 | 6/2001 | Rizo et al. |
| 6,289,235 B1 | 9/2001 | Webber et al. |
| 6,549,607 B1 | 4/2003 | Webber |
| 6,801,597 B1 | 10/2004 | Webber |
| 6,810,278 B1 | 10/2004 | Webber et al. |
| 2001/0034482 A1 | 10/2001 | Webber et al. |
| 2003/0026469 A1 | 2/2003 | Kreang-Arekul et al. |
| 2005/0059886 A1 | 3/2005 | Webber |

FOREIGN PATENT DOCUMENTS

| | | |
|---|---|---|
| AU | 738399 | 3/1999 |
| CA | 2134213 | 11/1993 |
| DE | 69330948 | 4/1992 |
| EP | 0638884 | 8/1994 |
| EP | 0638224 | 10/2001 |
| GB | 2016855 | 1/1979 |
| JP | 55-141097 | 11/1980 |
| JP | 59-197240 | 11/1984 |
| JP | 63-140907 | 9/1988 |
| JP | 01-276049 | 11/1989 |
| JP | 01-276597 | 11/1989 |
| JP | 02-42347 | 2/1990 |
| JP | 02-084984 | 3/1990 |
| JP | 02-104174 | 4/1990 |
| JP | 02-279141 | 11/1990 |
| JP | 03-132748 | 6/1991 |
| JP | 3639857 | 1/2005 |
| WO | 93/22893 | 1/1993 |
| WO | 94/23647 | 10/1994 |
| WO | 99/44503 | 9/1999 |

OTHER PUBLICATIONS

Tsuneo Saito, et al., "Three-Dimensional Quantitative Coronary Angiography", IEEE Transactions on Biomedical Engineering, vol. 37, No. 8, Aug. 1990, pp. 768-777.

"Proceedings of 14th Annual Meeting of the American Association of Physicists." vol. 17, No. 6, Jun. 26-29, 1972. Philadelphia, p. 878, R. Mohan et al., "A Computer-Assisted Rapid Method for source Localization in Interstitial Implants," abstract.

Webber et al., "Synthesis of Arbitrary X-Ray Projections from a Finite Number of Existing Projections," SPIE, vol. 535, 1985, p. 84-91.

Grant, D.G., "Tomosynthesis: A Three-Dimensional Radiographic Imaging Technique," IEEE Transactions on Bio-Medical Engineering, vol. BME-19, No. 1, Jan. 1972, pp. 20-28.

Ruttiman, U.E., et al., "Restoration of Digital Multiplane Tomosynthesis by a Constrained Iteration Method," IEEE Transactions on Medical Imaging, vol. ME-3, No. 3, Sep. 1984, pp. 141-148.

Ruttimann, U.E., et al., "An Opitmal Synthetic Aperture for Circular Tomosynthesis," Medical Physics, vol. 16, No. 3, May/Jun. 1989, pp. 398-405.

Webber et al., "Turned-apeture computer technology (TACT TM). Theory and application for three-dimensional dento-alveolar imaging," Dentomaxillofacial Radiology (1997) 26, pp. 53-62.

EVS-125 X-Ray Slicer Catalog, Yunihaito Co., Ltd., Shinjuku-KU, Tokyo (Japanese translation).

\* cited by examiner

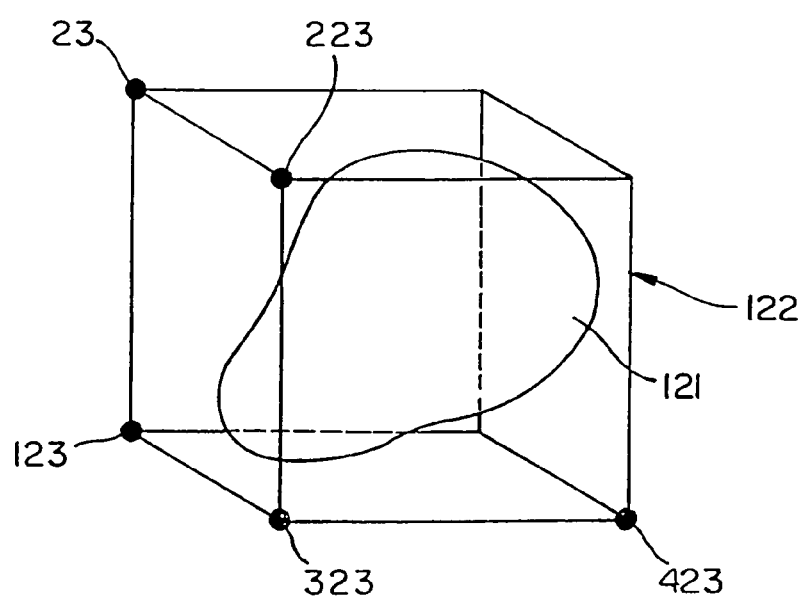
F I G. 5

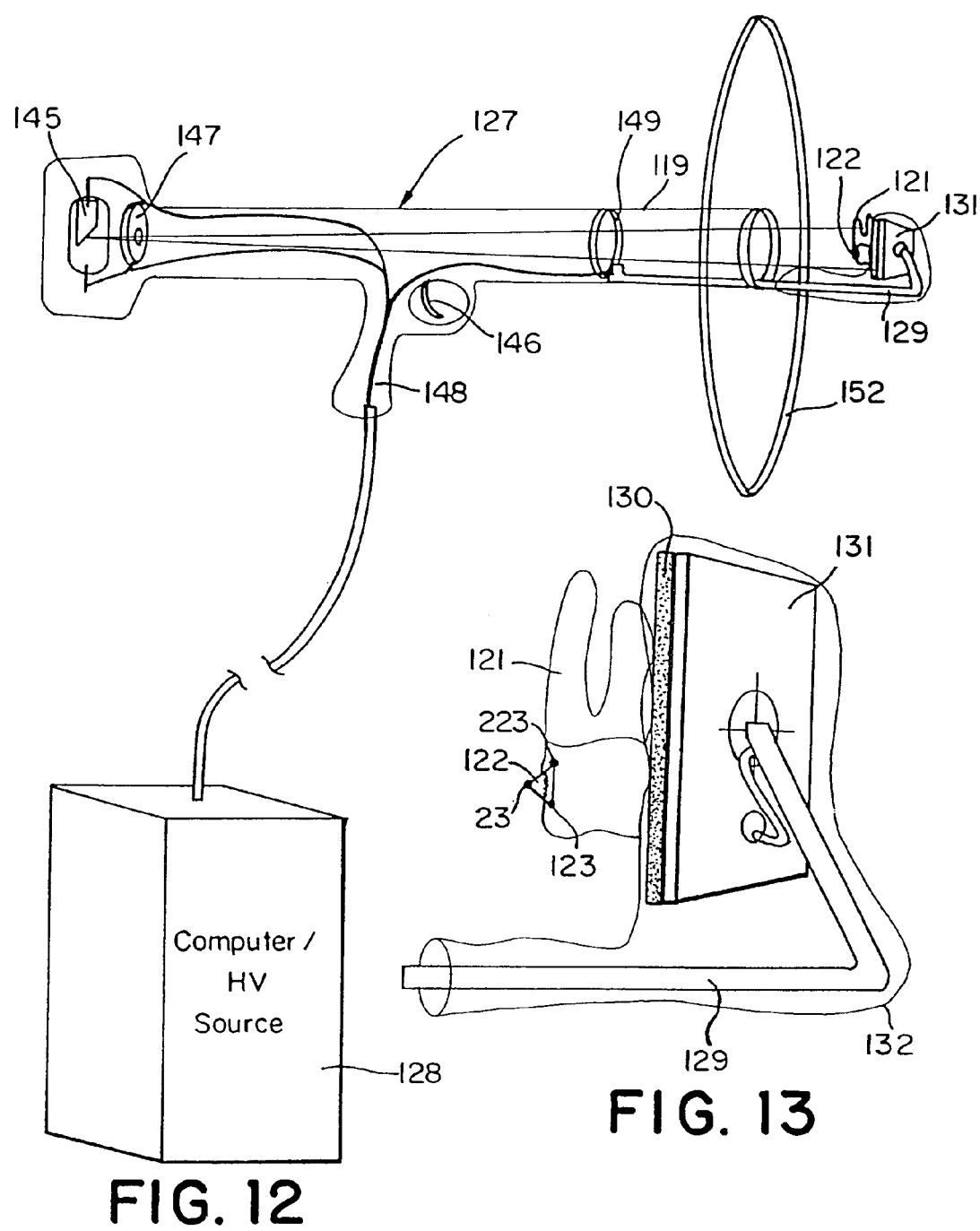

Example:

$a := 71$ $q := \dfrac{\pi}{100}, \dfrac{\pi}{99} \ldots \dfrac{\pi}{2}$ $c := 82$ $delta(a,q,c) := \dfrac{-1}{2} \cdot \dfrac{\left(c + 1 \cdot \sqrt{-a^2 \cdot \cos(q)^2 + a^2 \cdot \cos(q)^4} - c^2\right)}{(\sin(q) \cdot \cos(q))}$

METHOD AND SYSTEM FOR CREATING THREE-DIMENSIONAL IMAGES USING TOMOSYNTHETIC COMPUTED TOMOGRAPHY

RELATED APPLICATIONS

This application is a continuation of U.S. application Ser. No. 09/862,006, filed on May 21, 2001, now U.S. Pat. No. 6,810,278, which is a continuation of U.S. application Ser. No. 09/034,922, filed on Mar. 5, 1998, now U.S. Pat. No. 6,289,235, the subject matter of which applications is incorporated herein by reference.

FIELD OF THE INVENTION

The present invention relates to a method and system for creating three-dimensional displays or images from a multiplicity of two-dimensional projections and, more specifically, to a method and system for use in computed tomography systems in which random relative positional geometries between the source of radiation, the object of interest, and the recording means may be used for recording radiographic images for tomosynthesis.

BACKGROUND OF THE INVENTION

A wide range of tomosynthetic imaging techniques has previously been demonstrated to be useful in examining three-dimensional objects by means of radiation. These imaging techniques differ in the size and configuration of the effective imaging aperture. At one extreme, the imaging aperture approaches zero (i.e., a pinhole) and the resulting display is characterized by images produced from a single transmission radiograph. This yields an infinitely wide depth of field and therefore no depth information can be extracted from the image. At the other extreme, the aperture approaches a surrounding ring delimiting an infinite numerical aperture resulting in projection angles orthogonal to the long axis of the irradiated object. This yields an infinitely narrow depth of field and hence no information about adjacent slices through the object can be ascertained. It therefore follows that a "middle ground" approach, which provides the ability to adapt a sampling aperture to a particular task, would be highly advantageous.

The key to achieving the full potential of diagnostic flexibility lies in the fact that perceptually meaningful three-dimensional reconstructions can be produced from optical systems having any number of different aperture functions. That fact can be exploited since any aperture can be approximated by summation of a finite number of appropriately distributed point apertures. The key is to map all incrementally obtained projective data into a single three-dimensional matrix. To accomplish this goal, one needs to ascertain all positional degrees of freedom existing between the object of interest, the source of radiation, and the detector.

In the past, the relative positions of the object, the source, and the detector have been determined by fixing the position of the object relative to the detector while the source of radiation is moved along a predetermined path, i.e. a path of known or fixed geometry. Projective images of the object are then recorded at known positions of the source of radiation. In this way, the relative positions of the source of radiation, the object of interest, and the detector can be determined for each recorded image.

Previously, a method and system has been described which enables the source of radiation to be decoupled from the object of interest and the detector. This is accomplished by fixing the position of the object of interest relative to the detector and providing a fiducial reference which is in a fixed position relative to the coupled detector and object. The position of the image of the fiducial reference in the recorded image then can be used to determine the position of the source of radiation.

However, none of the existing techniques can be used in the most general application wherein the radiation source, the object of interest, and the detector are independently positioned for each projection. In such systems, there are nine possible degrees of freedom: 2 translational and 1 displacement degrees of freedom for the radiation source relative to the selected object and 2 translational, 1 displacement, 2 tilting, and 1 rotational degrees of freedom for the recording medium relative to the selected object. It is highly desirable to have a system and a method for constructing a three-dimensional radiographic display from two-dimensional projective data wherein the source of radiation, the object of interest, and the detector are all allowed to independently and arbitrarily vary in position relative to each other.

SUMMARY OF THE INVENTION

The present invention relates to an extension of tomosynthesis which facilitates three-dimensional reconstructions of an object from any number of arbitrary plane projections of the object produced from any number of arbitrary angles. The information required to produce the three-dimensional reconstructions is derived from fiducial analysis of the projections themselves or from analyses of functional relationships established through known fiducial constraints. In accordance with the present invention, a system and methods are provided for creating three-dimensional images using tomosynthetic computed tomography in which the system and methods significantly simplify the construction of image slices at selected slice positions through an object. Following a one-time transformation of a series of projected images, only simple offset and averaging operations are required in selected embodiments of the invention for a variety of subsequent reconstructions of a volumetric region within which projective variations may be considered negligible.

The system comprises an identifiable fiducial reference located in a fixed position relative to the object. The fiducial reference comprises at least two reference markers which are in a fixed geometry relative to each other. One of the reference markers may be used as an alignment marker during construction of a tomosynthetic slice through the object. The other reference marker or markers may be used to projectively warp or transform a projected image from an actual projection plane to a virtual projection plane. Each reference marker may be small enough to be considered point-size or, alternatively, may be finite in size. However, there are advantages to using markers of a known geometry such as spherical markers with a measurable diameter. In one embodiment, the fiducial reference comprises five point-size or finite reference markers that are arranged so that four of the reference markers are co-planar and no three or more reference markers are collinear.

A radiation source is provided for irradiating the object with the fiducial reference in a fixed position relative to the object. The preferred radiation source depends upon the particular application. For example, the present invention may be practiced using x-rays, electron microscopy, ultrasound, visible light, infrared light, ultraviolet light, microwaves, or virtual radiation simulated by manipulation of magnetic fields (magnetic resonance imaging (MRI)).

A recording medium or detector is used to record a series of projected images. Each projected image may include an object image of the object and a reference marker image for each of the reference markers. The recording medium may be in the form of a photographic plate or a radiation-sensitive, solid-state image detector such as a charge-coupled device (CCD), or any other system capable of producing two-dimensional projections or images suitable for digitization or other analysis.

In operation, the system of the present invention is used to synthesize a three-dimensional reconstruction of the object to obtain, for example, an image slice through the object, at a selected slice position through the object, from a plurality of projected images detected at the recording medium. The simplification of the construction method is achieved by warping, i.e. transforming or mapping, a series of projected images onto a virtual projection plane to yield modified images that would match those that would have been generated had the detector been in a fixed position relative to the object. By warping the projected images onto the virtual projection plane, the computation required for each image slice construction is greatly reduced. In addition, the solution of the projective transformations can be performed via a direct method that is both efficient and computationally robust. Further, magnification differences can be compensated for by appropriate scaling of the images.

A series of two-dimensional projected images of an object with an associated fiducial reference is recorded. The fiducial reference markers are coupled in fixed position relative to the object. The projected images can be recorded with (i) the source, (ii) the recording medium, and (iii) the fiducial reference markers coupled to the object, in various or arbitrary projection geometries. Further, the projection geometry preferably varies from projected image to projected image. Some variation is required to produce a finite depth of field.

The virtual projection plane may preferably correspond to the position of a plane through at least one of the reference markers in real space or to a plane defined by one of the existing projected images. Imaging systems that use projective geometries, which include optical and radiographic systems, can be appropriately warped using a projective transformation matrix. The projective transformation matrix is generated by solving each projected image relative to the virtual projection plane.

The resulting transformations compensate for magnification and/or projective differences between the various images. Such differences are introduced when the source is sufficiently close to the object and/or the source moves in a direction which is not parallel to the projection plane.

Once the projected images are warped and scaled to compensate for projective artifacts, construction of an image slice of the object at a selected slice position is performed based on techniques used in single reference marker applications. An example of such a technique is described in U.S. Pat. No. 5,359,637, which is incorporated herein by reference. Accordingly, the single reference point projection required by this technique may be abstracted from characteristics known to be associated with the object being projected, or from one or more fiducial reference markers either attached to or otherwise functionally related to the irradiated object.

BRIEF DESCRIPTION OF THE DRAWINGS

The foregoing summary, as well as the following detailed description of the preferred embodiments of the present invention, will be better understood when read in conjunction with the accompanying drawings, in which:

FIG. 5 is a schematic representation showing an arrangement of reference markers in accordance with the an embodiment of the present invention, wherein five spherical reference markers are positioned at five of the eight vertices of a cube;

FIG. 12 is a schematic representation of an embodiment of the present invention wherein the source is a hand-held X-ray source which is constrained relative to the recording medium by a C-arm;

FIG. 13 is an enlarged schematic representation of the object of interest and the recording medium depicted in FIG. 14;

FIG. 24 is a graph of the distance from the center of a reference marker to the source, $a_p$, versus the major diameter of the reference images, a;

FIG. 25 is a graph of the projection angle, θ, versus the major diameter of the reference images, a;

DETAILED DESCRIPTION OF THE PREFERRED EMBODIMENTS

Figure 1:
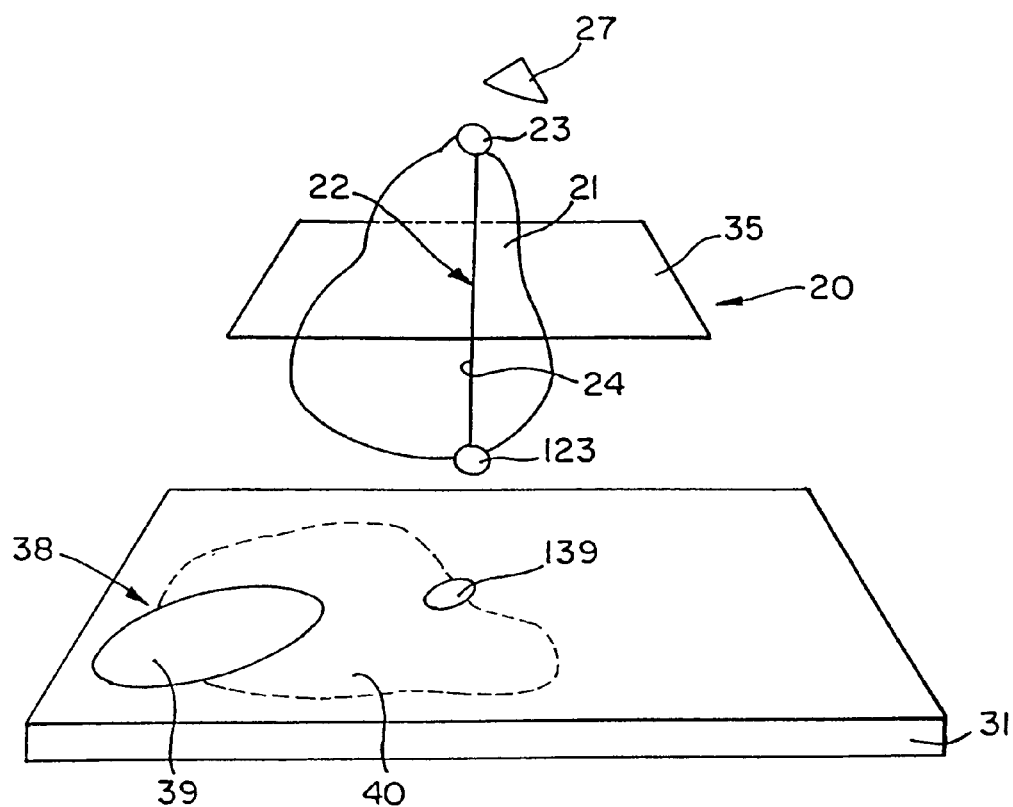
FIG. 1 is a schematic representation of a system for creating three-dimensional radiographic displays using computed tomography in accordance with the present invention.

The present invention generally relates to a system 20, as depicted schematically in FIG. 1, for synthesizing an image of an object 21 at a selected slice position 35 through the object 21 from a plurality of radiographic projected images 38 of the selected object 21. A fiducial reference 22 is held in a fixed position relative to the selected object 21, for example, by directly attaching the fiducial reference 22 to the object 21. The fiducial reference comprises two finite sized, identifiable reference markers, 23 and 123, which are maintained coupled together in a fixed geometry relative to each other by a radiolucent bar 24. However, the fiducial reference 22 may comprise various numbers and arrangements of reference markers 23. A radiation source 27 is provided to irradiate the object 21 along with the fiducial reference 22. Irradiation of the object 21 casts a projected image 38 onto a recording medium 31. The projected image 38 comprises an object image 40 of the object 21 and reference images, 39 and 139, of the reference markers, 23 and 123, respectively.

In general, the pattern of source 27 positions does not need to be in any fixed geometry or position. Indeed, the position of the source 27 may be totally arbitrary in translation and displacement relative to the object 21. Likewise, the recording medium 31 may also be arbitrarily movable relative to the object 21 by translation, displacement, tilting, or rotation. The only requirement is that for every degree of freedom in the system resulting from movement of the source 27 or the recording medium 31 relative to the object 21, the fiducial reference 22 must include sufficient measurable or defined characteristics, such as size, shape, or numbers of reference markers 23, to account for each degree of freedom.

The minimum number of reference markers required to completely determine the system depends on the constraints, if any, imposed on the relative positions of (1) the radiation source, (2) the object and fiducial reference, and (3) the recording medium. The system may have a total of nine possible relative motions (2 translations and 1 displacement for the radiation source relative to a desired projection plane and 2 translations, 1 displacement, 2 tilts, and 1 rotation for the recording medium relative to the desired projection plane). Each of these possible relative motions must be capable of analysis either by constraining the system and directly measuring the quantity, by providing a sufficient number of reference markers to enable the quantity to be determined, or by estimating the value of the quantity. Each unconstrained relative motion represents a degree of freedom for the system. For a system to be completely determined, the total number of degrees of freedom in the system must be less than or equal to the total number of degrees of freedom associated with the fiducial reference.

More than the minimum number of reference markers can be used. In such cases, the system is overdetermined and least squares fitting can be used to improve the accuracy of the resulting image slices. If, however, less than the minimum number of reference markers is used, then the system is underdetermined and the unknown degrees of freedom must either be estimated or measured directly.

Although the reference markers can be essentially any size and shape, spherical reference markers of known diameter may be used. When using spherical reference markers of a finite size, a single reference marker can account for up to five degrees of freedom. When a spherical reference marker is projected obliquely onto the recording medium, the reference image cast by the spherical reference marker is elliptical and is independent of any rotation of the reference marker. Determining the position of the reference image in the projection plane (X- and Y-coordinates) and the magnitudes of the major and minor diameters of the elliptical image accounts for four degrees of freedom. Further, when the distance between the radiation source and the reference marker is sufficiently short, the reference image will be magnified relative to the actual size of the reference marker, thereby accounting for an additional degree of freedom. In contrast, only two degrees of freedom (the X- and Y-coordinates) are typically associated with the reference image of a point-size reference marker.

Figure 4:
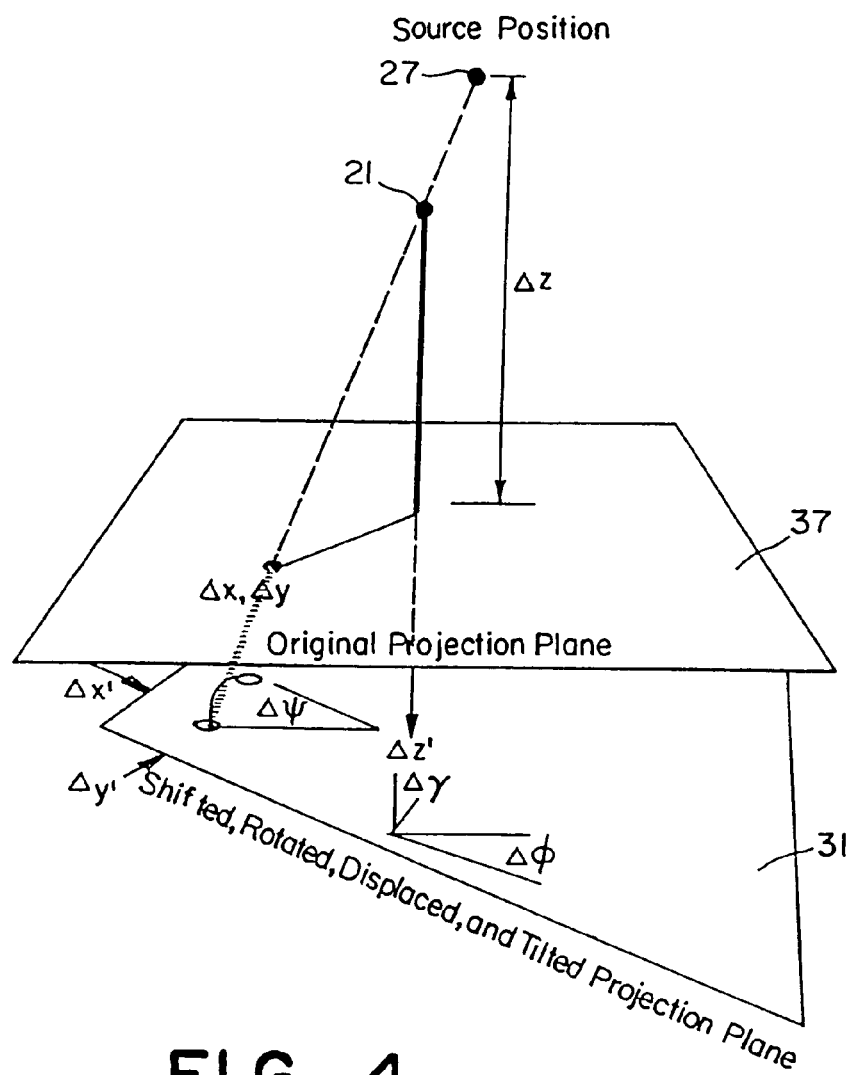
FIG. 4 is a schematic representation of a system having nine degrees of freedom in which a source is shifted and displaced relative to an original projection plane and in which a projection plane of a recording medium is shifted, rotated, displaced, and tilted relative to the original projection plane.

The most complex, yet most generally applicable, arrangement is depicted in FIG. 4, wherein the radiation source 27 and the recording medium 31 are completely unconstrained and uncoupled from the selected object 21. In this arrangement, there are nine degrees of freedom: 2 translational (ΔX and ΔY) and 1 displacement (ΔZ) degrees of freedom for the radiation source 27 relative to an original or desired projection plane 37 and 2 translational (ΔX' and ΔY'), 1 displacement (ΔZ'), 2 tilting (Δγ and ΔΦ), and 1 rotational (ΔΨ) degree of freedom for the recording medium 31 relative to the original or desired projection plane. Accordingly, a fiducial reference system sufficient to solve a projection system having nine degrees of freedom is needed to completely determine the system.

One embodiment of the present invention that permits this general arrangement to be realized conveniently involves two-dimensional projected images from a system comprised of a fiducial reference having five point-size or finite reference markers. This approach conveniently facilitates three-dimensional reconstructions when exactly four reference markers are coplanar and no three or more reference markers are collinear. Under these conditions, only the projection from the non-coplanar marker need be distinguished from the other four because the projections from the latter always bear a fixed sequential angular arrangement relative to each other which simplifies identification of homologous points in all projections. For example, the reference markers can be placed at five contiguous vertices of a cube as shown in FIG. 5. Fiducial reference 122 comprises five reference markers, 23, 123, 223, 323, 423, positioned contiguously at five vertices of a cube. The object 121 is preferably positioned within the cube. The four co-planar reference markers, 23, 123, 223, and 323, then can be used for projectively warping or transforming the projected images onto a desired projection plane while the remaining reference marker 423 serves as the alignment marker required to determine the normalized projection angle as described in U.S. Pat. No. 5,359,637.

The most general reconstruction task requiring information sufficient to determine all nine possible degrees of freedom requires computation of separate projective transformations for each projected image in each and every slice. However, by limiting the region of interest to a subvolume constrained such that the magnification across and between its slices may be considered constant, it is possible to generate veridical three-dimensional images within the volume much more efficiently. The increase in efficiency under these conditions results from the fact that all projections within this region can be mapped by a single fixed transformation, and that associated slice generation can be accomplished by simple tomosynthetic averaging of laterally shifted projections as described in U.S. Pat. No. 5,359,637.

Figure 11:
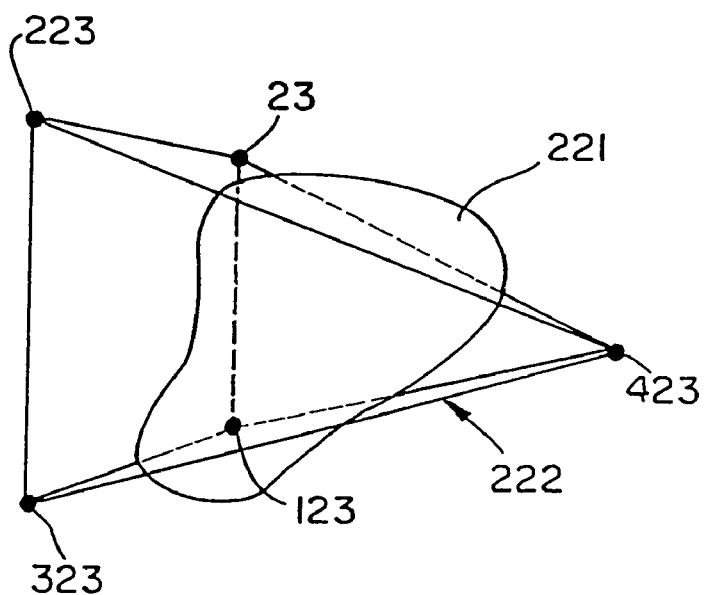
FIG. 11 is a schematic representation of an embodiment of the present invention wherein the reference markers of the fiducial reference are positioned at the vertices of a square pyramid.

Another useful arrangement of the fiducial reference comprising five reference markers is shown in FIG. 11, wherein a fiducial reference 222 employing a pyramidal distribution of reference markers 323 is used. The fiducial reference 222 comprises five reference markers 23, 123, 223, 323, and 423, which are held in a fixed relationship relative to each other and to the object 221. As was the case in FIG. 5, four of the reference markers, 23, 123, 223, and 323, lie in a plane that can be used to establish the desired projection plane. Here, they define the four corners of the base of a pyramid. The fifth reference marker 423 is positioned to define the apex of the pyramid and serves as the means for determining the projection angles relative to the desired projection plane as described in U.S. Pat. No. 5,359,637. In use, the fiducial reference 222 may be attached or fixed relative to the object 221 such that the base of the pyramid is proximate to the recording medium and the apex of the pyramid is proximate to the source.

Figure 15:
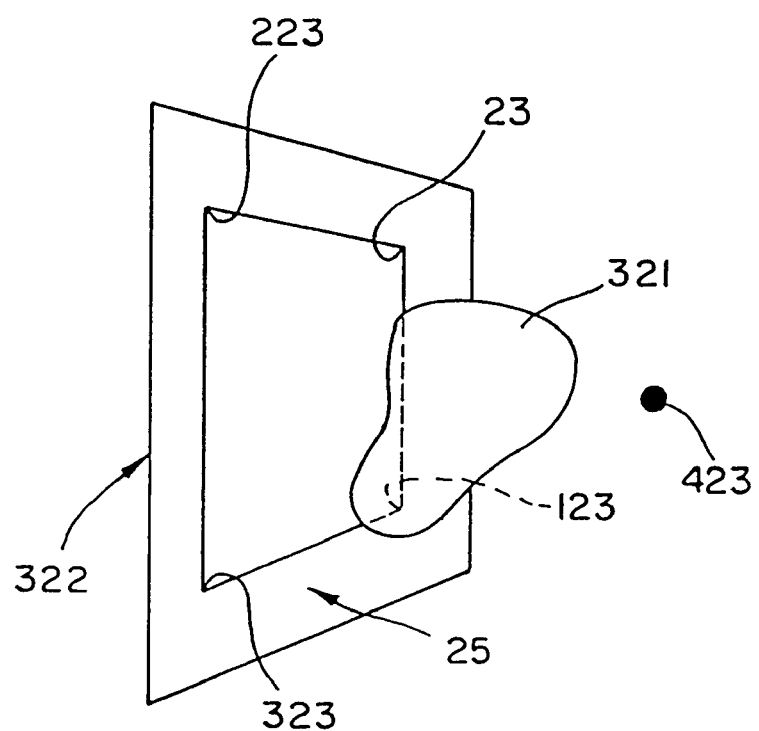
FIG. 15 is a schematic representation of an embodiment of the present invention wherein the corners of a frame define four reference markers.

In FIG. 15, a fiducial reference 322 having an alternative arrangement of reference markers in a pyramidal distribution is shown. In this arrangement, the fiducial reference 322 comprises a radiopaque frame 25 having a radiolucent central window. The four inside corners of the radiopaque frame 25 define four reference markers, 23, 123, 223, and 323, at the base of the pyramid. The fifth reference marker 423 is positioned at the apex of the pyramid. Preferably, the object 321 is positioned between the frame 25 and the reference marker 423.

Figure 14:
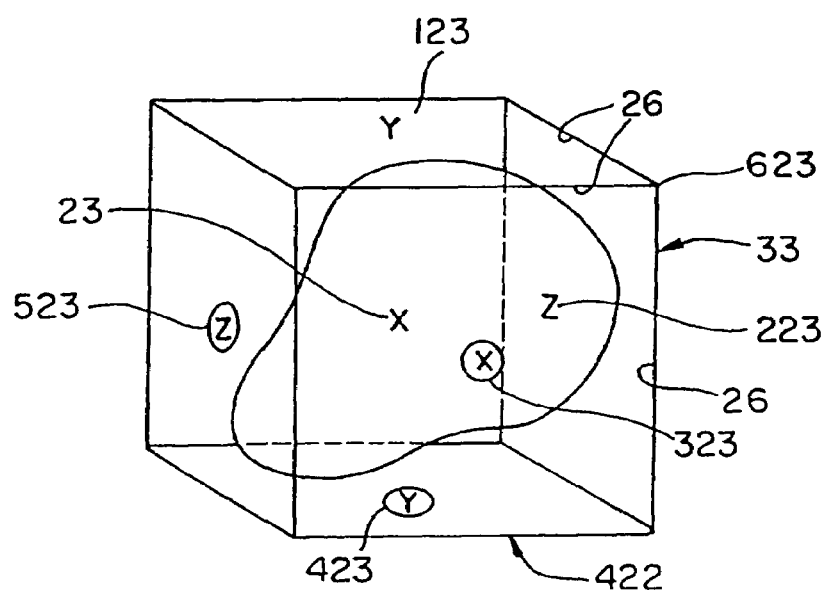
FIG. 14 is a schematic representation of an embodiment of the present invention wherein the reference markers of the fiducial reference are positioned at the centers of the faces of a parallelepiped.

In FIG. 14, a fiducial reference 422 which is also useful for solving a system with nine degrees of freedom is shown. Fiducial reference 422 comprises a rectangular parallelepiped 33 with radiopaque reference markers, 23, 123, 223, 323, 423, and 523, centered on each of the six faces of the parallelepiped 33. The reference markers, 23, 123, 223, 323, 423, and 523, are marked with distinguishable indicia, such as X, Y, Z, $\widehat{X}$, $\widehat{Y}$, and $\widehat{Z}$ so that the reference images cast by the markers, 23, 123, 223, 323, 423, and 523, can be identified easily and distinguished from one another. Alternatively or additionally, two or more of the edges of the parallelepiped 33 may be defined by radiopaque bars 26 such that the intersections of the bars 26 provide additional reference markers, such as reference marker 623 located at the intersection of the three bars labeled 26 in FIG. 14. [HRt] Reducing the uncertainty of the projection geometry through the constraint of one or more degrees of freedom reduces the complexity of the resulting reconstruction. An arrangement of the system of the present invention which is somewhat constrained is depicted in FIGS. 12 and 13, wherein a hand-held X-ray source is provided such that the orthogonal distance between the radiation source 127 and the recording medium 131 is fixed by a C-arm 129 at a distance short enough so that the image cast by the fiducial reference 122 is magnified relative to the size of the actual fiducial reference 122. Preferably, the C-arm 129 is connected to the recording medium 131 by a concentric swivel collar 149 to allow the C-arm 129 to be rotated relative to the recording medium 131. A disposable and crushable radiolucent foam cushion 130 may be attached to the surface of the recording medium 131 to permit comfortable customized stable adaptation of the detector 131 to the object 121. The other end of the C-arm 129 is attached to a potted X-ray source 145 so that radiation emanating from the potted X-ray source 145 impinges upon the recording medium 131. A trigger 146 is provided for operating the source 127. The source 127 optionally comprises a circular beam collimator 147 for collimating radiation emanating from the source 127. The collimator 147 may provide a relatively long focal-object distance to provide nearly affine projection geometries. Preferably, a handle 148 is also provided to enable the operator to more easily maneuver the source 127. The hand-held X-ray source 127 is connected to a computer/high voltage source 128 for controlling operation of the device. In addition, a disposable plastic bag 132 can be positioned around the detector 131 for microbial isolation. The source 127 can optionally comprise a rotatable transparent radiopaque plastic cylinder 119 and a transparent radiopaque shield 152 to protect the operator from scattered radiation. In this arrangement, there are 3 degrees of freedom (two translational and one displacement for the radiation source 127). Accordingly, a fiducial reference compensating for at least three degrees of freedom is necessary to completely describe or analyze the system. One convenient embodiment for solving the system depicted in FIGS. 12 and 13 employs a fiducial reference 122 comprising a single radiopaque sphere of finite diameter. Under those conditions, the length of the minor axis of the resulting elliptical shadow plus two translational measurements are sufficient to define the projection geometry completely.

Figure 17:
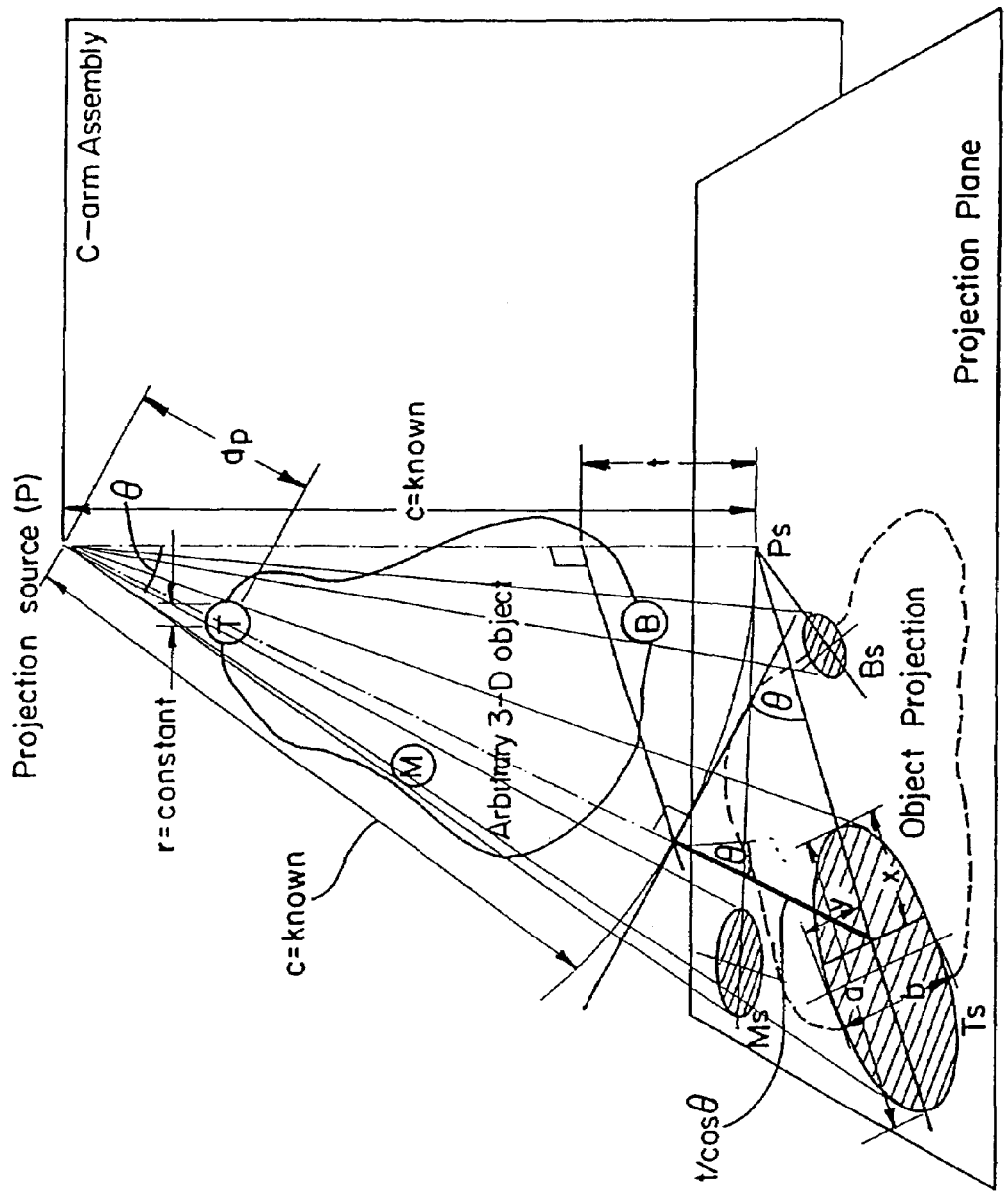
FIG. 17 is a schematic representation of the parameters associated with a system comprising three spherical, non-collinear reference markers wherein the orthogonal distance between the radiation source and the recording medium is fixed at a distance short enough so that the images cast by the reference markers are magnified relative to the size of the actual reference markers.
Figure 18:
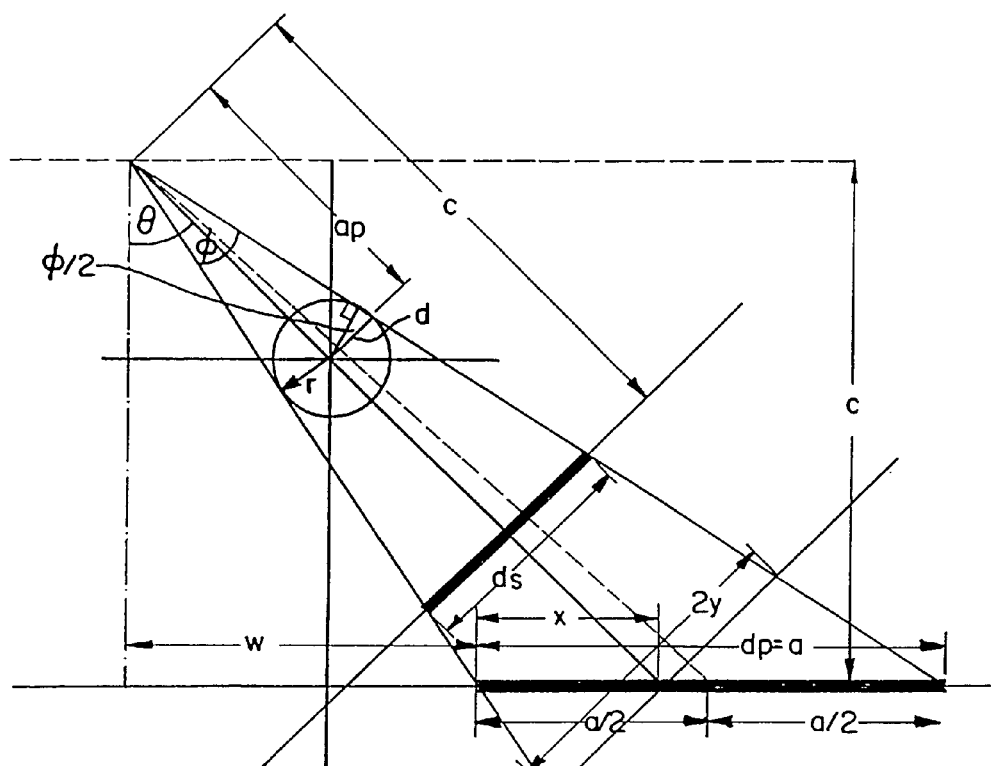
FIG. 18 is a schematic representation of the relevant parameters associated with a reference image associated with a spherical reference marker.
Figure 19:
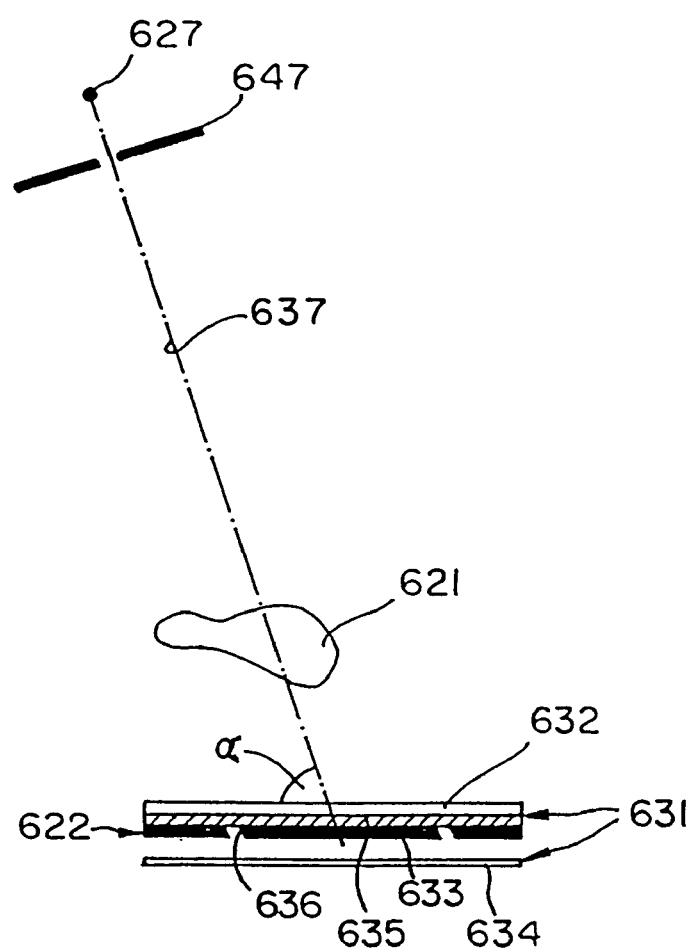
FIG. 19 is a schematic representation of an embodiment of the present invention wherein the fiducial reference comprises a radiopaque shield with a ring-like aperture.
Figure 25:
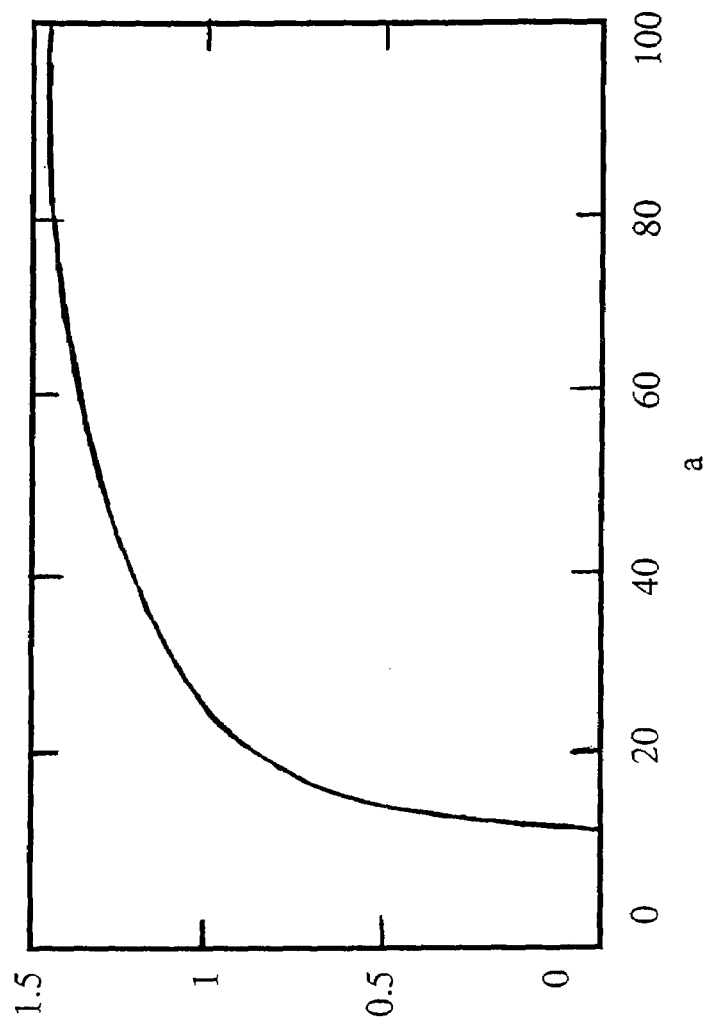
Figure 26:
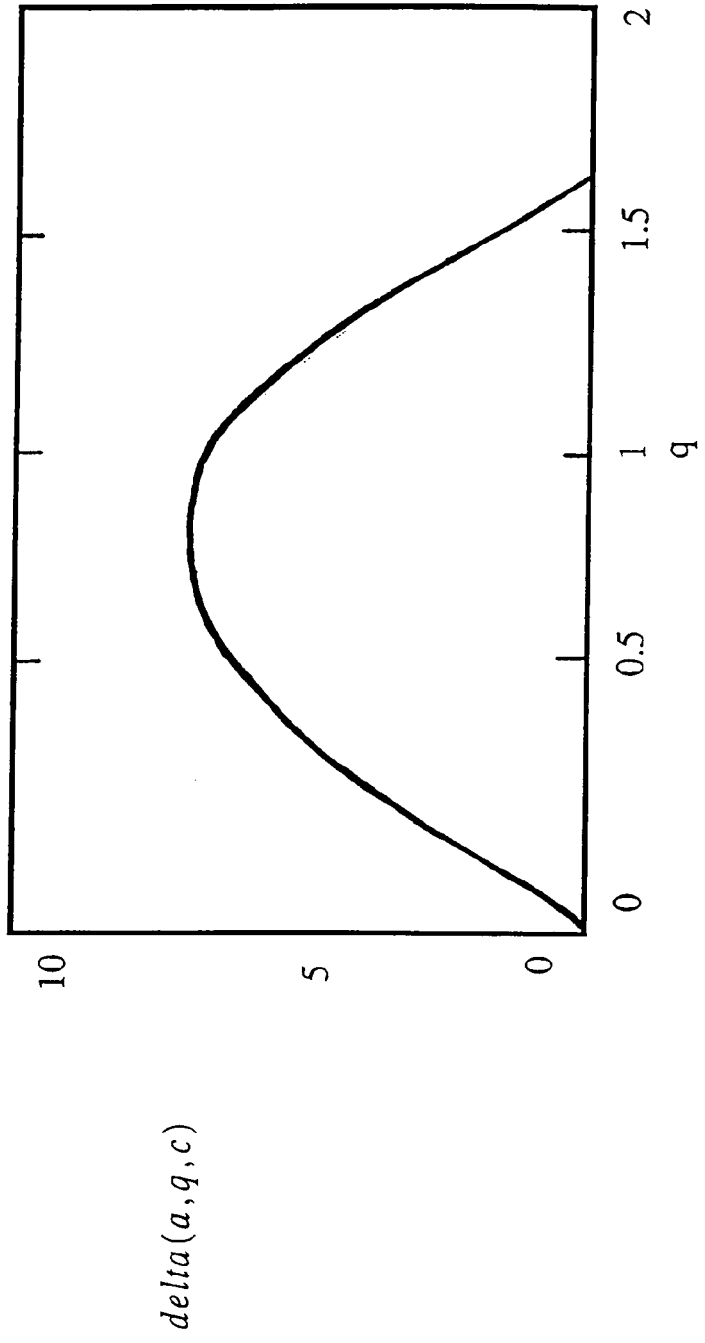
FIG. 26 is a graph of the offset correction distance, delta, versus the projection angle, q.

The computational steps involved in synthesizing a three-dimensional image using three spherical, non-linear reference markers in a system wherein the orthogonal distance between the radiation source and the recording medium is fixed at a distance short enough so that the images cast by the reference markers are magnified relative to the size of the actual reference markers (i.e., a system with eight degrees of freedom as depicted in FIGS. 12 and 13) can be derived with reference to FIGS. 17 and 19. In the drawings, c is the fixed distance between the source and the projection plane; $P_s$ is the orthogonal projection of the source onto the projection plane; B, M, and T are the reference markers; r is the radius of the reference markers; $a_p$ is the distance from the center of a reference marker to the source; θ is the angle subtended by the center of a reference marker relative to a line orthogonal to the projection plane through the source; φ is the angle at the apex of an isosceles triangle having a base of length r and a height of length $a_p$; $B_s$, $M_s$, and $T_s$ are the reference images associated with the reference markers; a (or, alternatively, $d_p$) is the major diameter of the reference images; b is the minor diameter of the reference images; x is the length of a section of an arc associated with a reference image measured from the projection of the center of the corresponding reference marker onto the projection plane along the major diameter, b, in a direction toward $P_s$; y is the length of an arc associated with a reference image through the projection of the center of the corresponding reference marker onto the projection plane and parallel to the minor diameter of the reference image; and $d_s$ is the major diameter of a reference image in a virtual projection plane. The derivation of the solution to the system depicted in FIGS. 17 and 18 is attached hereto as Chart A and accompanying FIGS. 23–28. FIG. 25 illustrates a graph of the solution for the projection angle, theta, and FIG. 26 illustrates a graph of the solution for the offset correction distance, delta.

CHART A $a = d_p$   $2y = d_s(c + t/\cos\theta)/c$   $t = c(1 - \cos\theta)$ $d_p = \{\tan[\theta + \arctan(d_s/2c)] - \tan[\theta - \arctan(d_s/2c)]\}c$ $a_p = \dfrac{r}{\sin\dfrac{\theta}{2}} = \dfrac{r}{\sin\left(\arctan\dfrac{d_s}{2c}\right)}$   $d_s = \left\{2\tan\left[\arctan\dfrac{(x - c\tan\theta)}{c}\right] + \theta\right\}c$ $x = \dfrac{a\sin\theta\cos\theta + c + i\sqrt{a^2\cos\theta^4 - a^2\cos\theta^2 - c^2}}{2\sin\theta\cos\theta}$ Therefore, $a_p$ is $f'cn$ of $r$, $c$, $\theta$, and $a$ $\tan\left(\theta + \dfrac{\phi}{2}\right) = \dfrac{d_p + w}{c}$   $\sin\dfrac{\phi}{2} = \dfrac{r}{a_p}$ $\tan\left(\theta - \dfrac{\phi}{2}\right) = \dfrac{w}{c}$   $\cos\dfrac{\phi}{2} = \dfrac{r}{d}$ $\therefore \tan\left(\theta + \dfrac{\phi}{2}\right) = \dfrac{d_p + \tan\left(\theta - \dfrac{\phi}{2}\right)c}{c}$   $\therefore \tan\dfrac{\phi}{2} = \dfrac{d}{a_p}$ $d_p = \left[\tan\left(\theta + \dfrac{\phi}{2}\right) - \tan\left(\theta - \dfrac{\phi}{2}\right)\right]c$   $\dfrac{a_p}{2d} = \dfrac{c}{d_s}$ $\therefore \boxed{d_p = \left[\tan\left(\theta + \arctan\dfrac{d_s}{2c}\right) - \tan\left(\theta - \arctan\dfrac{d_s}{2c}\right)\right]c}$ $\therefore \dfrac{\phi}{2} = \arctan\dfrac{d_s}{2c}$ $\tan\theta = \dfrac{x + w}{c}$   $\therefore \boxed{x = c\left\{\tan\theta - \tan\left[\theta - \arctan\left(\dfrac{d_s}{2c}\right)\right]\right\}}$ $\boxed{a = c\left[\tan\left(\theta + \arcsin\dfrac{r}{a_p}\right) - \tan\left(\theta - \arcsin\dfrac{r}{a_p}\right)\right]}$ $\tan\left(q + \dfrac{1}{2}f\right) = \dfrac{dp + w}{c}$   #1

$\tan\left(q - \dfrac{f}{2}\right) = \dfrac{w}{c}$   #2

Solving #2 for $w$ and substituting the result into #1 yields:

$\tan\left(q + \dfrac{1}{2} \cdot f\right) = \dfrac{\left(dp - \tan\left(-q + \dfrac{1}{2} \cdot f\right) \cdot c\right)}{c}$   #3

Solving #3 for $dp$ yields:

$dp = \left(\tan\left(q + \dfrac{1}{2} \cdot f\right) + \tan\left(-q + \dfrac{1}{2} \cdot f\right)\right) \cdot c$   #4

$\sin\left(\dfrac{f}{2}\right) = \dfrac{r}{ap}$   #5

$\cos\left(\dfrac{f}{2}\right) = \dfrac{r}{d}$   #6

Dividing #5 by #6 yields:

$\tan\left(\dfrac{f}{2}\right) = \dfrac{d}{ap}$   #7

$\dfrac{ap}{2 \cdot d} = \dfrac{c}{ds}$   #8

Solving #7 for $d$ and substituting the result into #8 yields:

$\dfrac{1}{\left(2 \cdot \tan\left(\dfrac{1}{2} \cdot f\right)\right)} = \dfrac{c}{ds}$   #9

Solving #9 for $f/2$ yields:

$\dfrac{f}{2} = a\tan\left(\dfrac{ds}{2 \cdot c}\right)$   #10

Substituting #10 into #4 yields:

$dp = \left(\tan\left(q + a\tan\left(\dfrac{ds}{2 \cdot c}\right)\right) + \tan\left(-q + a\tan\left(\dfrac{ds}{2 \cdot c}\right)\right)\right) \cdot c$   #11

Solving #11 for $q$

Guess value: $q := 1$

Given $dp = \left(\tan\left(q + a\tan\left(\dfrac{ds}{2 \cdot c}\right)\right) + \tan\left(-q + a\tan\left(\dfrac{ds}{2 \cdot c}\right)\right)\right) \cdot c$ Angle($dp$, $ds$, $c$) : Find($q$)

Example: $dp := 10, 11 \ldots 100$ $ds := 10$ $c := 100$

Figure 23:
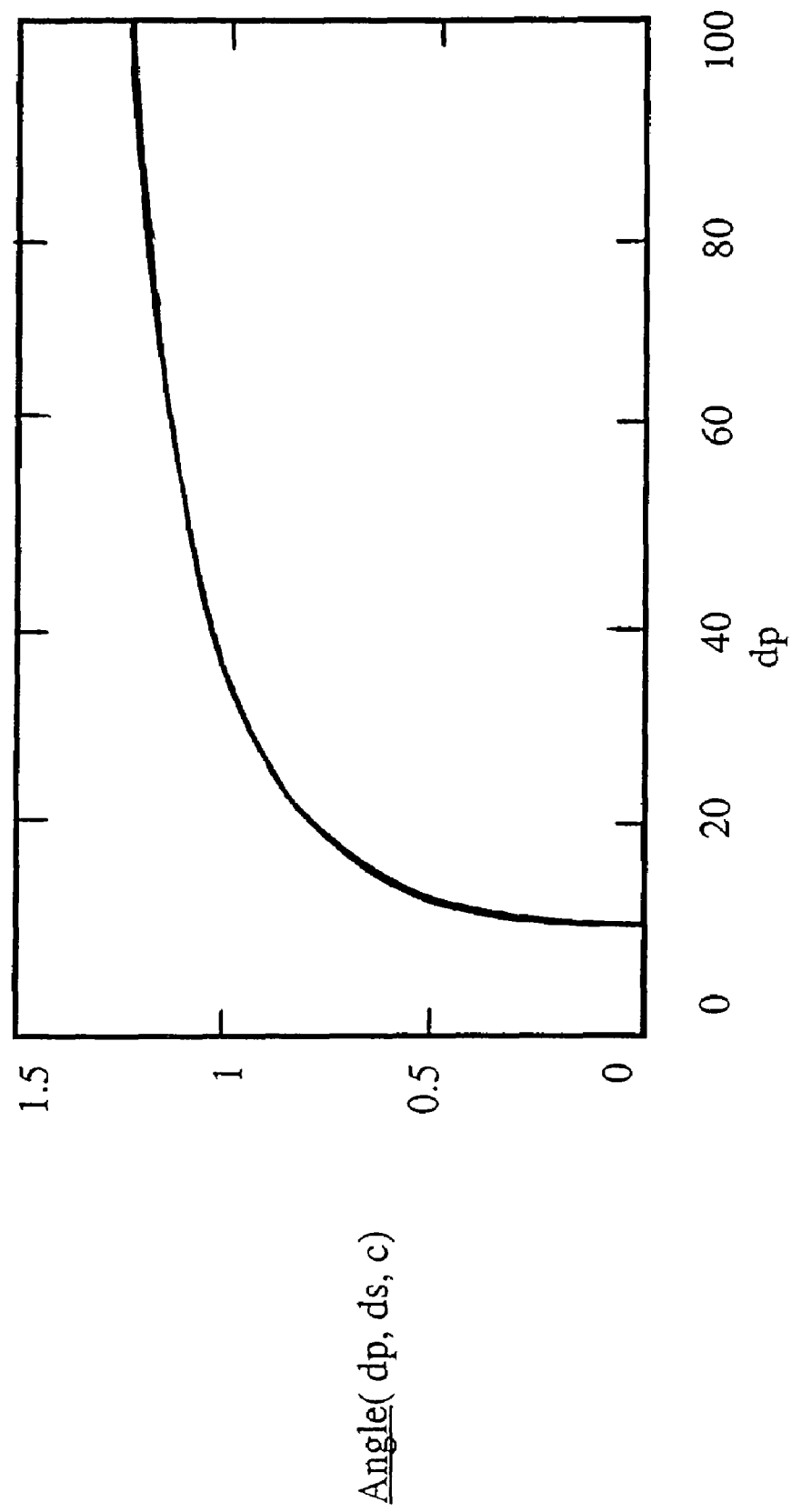
FIG. 23 is a graph of the projection angle, q, versus the major diameter of the reference image, $d_p$.

The result is shown in the graph of FIG. 23.

| dp | Angle (dp, ds, c) |
| --- | --- |
| 10 | $2.776 \cdot 10^{-5}$ |
| 11 | 0.306 |
| 12 | 0.42 |
| 13 | 0.5 |
| 14 | 0.563 |
| 15 | 0.615 |
| 16 | 0.658 |

-continued

| dp | Angle (dp, ds, c) |
|---|---|
| 17 | 0.696 |
| 18 | 0.729 |
| 19 | 0.758 |
| 20 | 0.784 |
| 21 | 0.808 |
| 22 | 0.83 |
| 23 | 0.849 |
| 24 | 0.868 |
| 25 | 0.885 |
| 26 | 0.9 |
| 27 | 0.915 |
| 28 | 0.929 |
| 29 | 0.941 |
| 30 | 0.954 |
| 31 | 0.965 |
| 32 | 0.976 |
| 33 | 0.986 |
| 34 | 0.996 |
| 35 | 1.005 |
| 36 | 1.014 |
| 37 | 1.022 |
| 38 | 1.03 |
| 39 | 1.038 |
| 40 | 1.045 |
| 41 | 1.052 |
| 42 | 1.059 |
| 43 | 1.065 |
| 44 | 1.072 |
| 45 | 1.078 |
| 46 | 1.083 |
| 47 | 1.089 |
| 48 | 1.094 |
| 49 | 1.1 |
| 50 | 1.105 |
| 51 | 1.11 |
| 52 | 1.114 |
| 53 | 1.119 |
| 54 | 1.123 |
| 55 | 1.128 |
| 56 | 1.132 |
| 57 | 1.136 |
| 58 | 1.14 |
| 59 | 1.144 |

Derivation of $x$ $$\tan(q) = \frac{x + w}{c} \quad \#1$$

$$c \cdot \tan\left(q - \frac{f}{2}\right) = w \quad \#2$$

$$\frac{f}{2} = a\tan\left(\frac{ds}{2 \cdot c}\right) \quad \#3$$

Substituting #3 into #2 yields:

$$c \cdot \tan\left(q - a\tan\left(\frac{ds}{2 \cdot c}\right)\right) = w \quad \#4$$

Substituting #4 into #1 yields:

$$\tan(q) = \frac{\left(x + c \cdot \tan\left(q - a\tan\left(\frac{1}{2} \cdot \frac{ds}{c}\right)\right)\right)}{c} \quad \#5$$

Solving #5 for $x$ yields:

$$x = \left(\tan(q) - \tan\left(q - a\tan\left(\frac{1}{2} \cdot \frac{ds}{c}\right)\right)\right) \cdot c \quad \#6$$

Equation of an ellipse expressed in terms of $x$, $y$, $a$, & $b$:

$$\frac{\left(\frac{a}{2} - x\right)^2}{\left(\frac{a}{2}\right)^2} + \frac{y^2}{\left(\frac{b}{2}\right)^2} = 1 \quad \#1$$

Solving #1 for positive values of $y$ yields:

$$y = b \cdot \sqrt{x} \cdot \frac{\sqrt{a - x}}{a} \quad \#2$$

Figure 27:
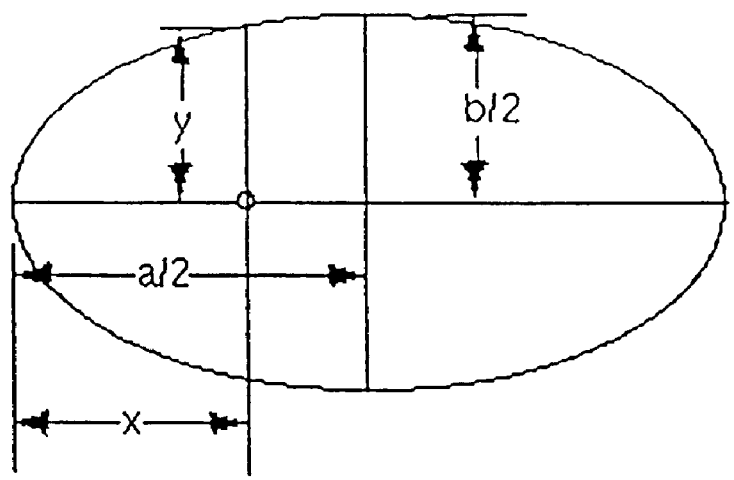
FIG. 27 is a graph of an ellipse showing the variables x, y, b/2, and a/2.

Let:

$x := 0, 0.1 \ldots 2$
$a := 4$
$b := 2$ as shown in FIG. 27.

Figure 28:
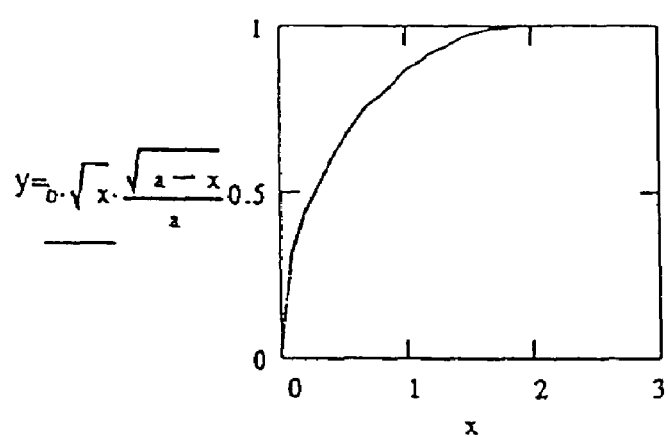
FIG. 28 is a graph of a plot of y versus x for the equation of the ellipse shown in FIG. 27.

Plotting y as a function of x, as shown in FIG. 28, yields:

| x | $y = b \cdot \sqrt{x} \cdot \frac{\sqrt{a-x}}{a}$ |
|---|---|
| 0 | 0 |
| 0.1 | 0.312 |
| 0.2 | 0.436 |
| 0.3 | 0.527 |
| 0.4 | 0.6 |
| 0.5 | 0.661 |
| 0.6 | 0.714 |
| 0.7 | 0.76 |
| 0.8 | 0.8 |
| 0.9 | 0.835 |
| 1 | 0.866 |
| 1.1 | 0.893 |
| 1.2 | 0.917 |
| 1.3 | 0.937 |
| 1.4 | 0.954 |
| 1.5 | 0.968 |
| 1.6 | 0.98 |
| 1.7 | 0.989 |
| 1.8 | 0.995 |
| 1.9 | 0.999 |
| 2 | 1 |

Derivation of $ap$ in terms of observable quantities $$ap = \frac{r}{\sin\left(\frac{f}{2}\right)} \quad \#1$$

$$a = \left[\tan\left[q + \left(\frac{f}{2}\right)\right] - \tan\left[q - \left(\frac{f}{2}\right)\right]\right] \cdot c \quad \#2$$

Solving #1 for $f/2$ yields:

$$f/2 = a\sin\left(\frac{r}{ap}\right) \quad \#3$$

Substituting #3 into #2 yields the following implicit equation:

$$a = \left(\tan\left(q + a\sin\left(\frac{r}{ap}\right)\right) - \tan\left(q - a\sin\left(\frac{r}{ap}\right)\right)\right) \cdot c \quad \#4$$

-continued

Guess value: $ap := 20$

Given $$a = \left(\tan\left(q + a\sin\left(\frac{r}{ap}\right)\right) - \tan\left(q - a\sin\left(\frac{r}{ap}\right)\right)\right) \cdot c$$

$ap(a, q, r, c) := \text{Find}(ap)$

Example:

$a := 50, 51 \ldots 100$
$q := \frac{\pi}{4}$
$r := 9$
$c := 82$

Figure 24:
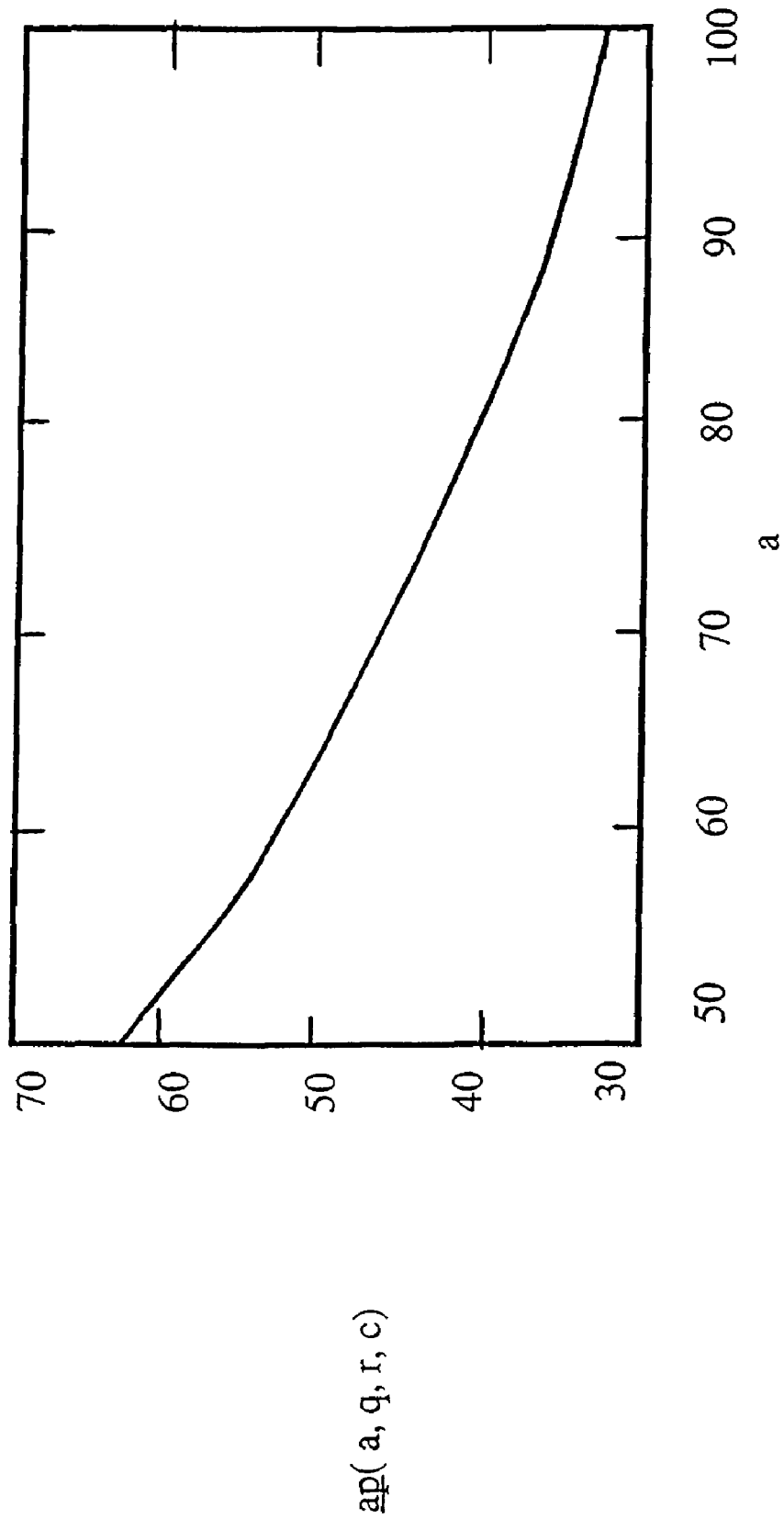

The solution for these values is plotted in FIG. 24.

Augmented Complex General Sphere Derivation $$dp = \left(\tan\left(q + a\tan\left(\frac{ds}{2 \cdot c}\right)\right) + \tan\left(-q + a\tan\left(\frac{ds}{2 \cdot c}\right)\right)\right) \cdot c \quad \#1$$

$a = dp \quad \#2$

Substituting #2 into #1 yields:

$$a = \left(\tan\left(q + a\tan\left(\frac{ds}{2 \cdot c}\right)\right) + \tan\left(-q + a\tan\left(\frac{ds}{2 \cdot c}\right)\right)\right) \cdot c \quad \#3$$

$$2 \cdot y = ds \cdot \frac{c + \frac{t}{\cos(q)}}{c} \quad \#4$$

Solving #4 for $ds$ and substituting the result into #3 yields:

$$a = \left[\tan\left[q - a\tan\left[\frac{y}{\left[\left(-1 - \frac{1}{c} \cdot \frac{t}{\cos(q)}\right) \cdot c\right]}\right]\right] + \tan\left[-q - a\tan\left[\frac{y}{\left[\left(-1 - \frac{1}{c} \cdot \frac{t}{\cos(q)}\right) \cdot c\right]}\right]\right]\right] \cdot c \quad \#5$$

$t = c \cdot (1 - \cos(q)) \quad \#6$

Substituting #6 into #5 and simplifying yields:

$$a = \left[\tan\left[q - a\tan\left[\frac{y}{\left[\left[-1 - \frac{(1-\cos(q))}{\cos(q)}\right] \cdot c\right]}\right]\right] + \tan\left[-q - a\tan\left[\frac{y}{\left[\left[-1 - \frac{(1-\cos(q))}{\cos(q)}\right] \cdot c\right]}\right]\right]\right] \cdot c \quad \#7$$

From the ellipse derivation ...

$$y = b \cdot \sqrt{x} \cdot \frac{\sqrt{a-x}}{a} \quad \#8$$

Substituting #8 into #7 yields:

$$\left[a = \left[\tan\left[q - a\tan\left[b \cdot \sqrt{x} \cdot \frac{\sqrt{a-x}}{\left[a \cdot \left[\left[-1 - \frac{(1-\cos(q))}{\cos(q)}\right] \cdot c\right]\right]}\right]\right] + \right.\right.$$
$$\left.\left.\tan\left[-q - \tan\left[b \cdot \sqrt{x} \cdot \left[\frac{\sqrt{a-x}}{\left[a \cdot \left[\left[-1 - \frac{(1-\cos(q))}{\cos(q)}\right] \cdot c\right]\right]}\right]\right]\right]\right] \cdot c \quad \#9$$

From the derivation of $x$ ...

$$x = \left(\tan(q) - \tan\left(q - a\tan\left(\frac{1}{2} \cdot \frac{ds}{c}\right)\right)\right) \cdot c \quad \#10$$

Solving #10 for $ds$ yields:

$$ds = 2 \cdot \tan\left[a\tan\left[\frac{(x - c \cdot \tan(q))}{c}\right] + q\right] \cdot c \quad \#11$$

Substituting #11 into #3 yields $$a = \left[\tan\left[2 \cdot q + a\tan\left[\frac{(x - c \cdot \tan(q))}{c}\right]\right] + \frac{(x - c \cdot \tan(q))}{c}\right] \cdot c \quad \#12$$

Solving #12 for $x$ & simplifying yields:

$$x = \begin{bmatrix} \frac{1}{2} \cdot \frac{(a \cdot \sin(q) \cdot \cos(q) + c + i \cdot \sqrt{-a^2 \cdot \cos(q)^2 + a^2 \cdot \cos(q)^4 - c^2})}{(\sin(q) \cdot \cos(q))} \\ \frac{1}{2} \cdot \frac{(a \cdot \sin(q) \cdot \cos(q) + c - i \cdot \sqrt{-a^2 \cdot \cos(q)^2 + a^2 \cdot \cos(q)^4 - c^2})}{(\sin(q) \cdot \cos(q))} \end{bmatrix} \quad \#13$$

Substituting the first solution of #13 into #9 yields:

$$a = \left[\tan\left[q - a\tan\left[\frac{1}{2} \cdot b \cdot \sqrt{2} \cdot \frac{\sqrt{\frac{a \cdot \sin(q) \cdot \cos(q) + c + i \cdot \sqrt{-a^2 \cdot \cos(q)^2 + a^2 \cdot \cos(q)^4 - c^2}}{(\sqrt{\sin(q)} \cdot \sqrt{\cos(q)})}}}{\left[a \cdot \left[\left[-1 - \frac{(1-\cos(q))}{\cos(q)}\right] \cdot c\right]\right]}\right]\right] \cdot c + $$

$$\left[\tan\left[-q - a\tan\left[\frac{1}{2} \cdot b \cdot \sqrt{2} \cdot \frac{\sqrt{\frac{a \cdot \sin(q) \cdot \cos(q) + c + i \cdot \sqrt{-a^2 \cdot \cos(q)^2 + a^2 \cdot \cos(q)^4 - c^2}}{(\sqrt{\sin(q)} \cdot \sqrt{\cos(q)})}}}{\sqrt{a - \frac{1}{2} \cdot \frac{\sqrt{-a^2 \cdot \cos(q)^2 + a^2 \cdot \cos(q)^4 - c^2}}{(\sin(q) \cdot \cos(q))}}}\right]\right] \cdot c \quad \#14$$

$\text{delta} = \frac{a}{2} - x \quad \#15$

Substituting the first solution of #13 into #15 and simplifying yields:

$$\text{delta} = \frac{-1}{2} \cdot \frac{\left(c + i \cdot \sqrt{-a^2 \cdot \cos(q)^2 + a^2 \cdot \cos(q)^4 - c^2}\right)}{(\sin(q) \cdot \cos(q))} \quad \#16$$

-continued

Solving #14 for $q$

Guess value:

Given $$a = \left| \tan \left[ q - a\tan \left[ \frac{1}{2} \cdot b \cdot \sqrt{2} \cdot \frac{\sqrt{a \cdot \sin(q) \cdot \cos(q) + c + i \cdot \frac{\sqrt{-a^2 \cdot \cos(q)^2 + a^2 \cdot \cos(q)^4 - c^2}}{(\sqrt{\sin(q)} \cdot \sqrt{\cos(q)})}}}{} \right] \right] \right.$$

$$\left. \sqrt{a - \frac{1}{2} \cdot \frac{\sqrt{-a^2 \cdot \cos(q)^2 + a^2 \cdot \cos(q)^4 - c^2}}{(\sin(q) \cdot \cos(q))}} \cdot \left[a \cdot \left[\left[-1 - \frac{(1-\cos(q))}{\cos(q)}\right] \cdot c\right]\right] \right| c +$$

$$\left| \tan\left[-q - a\tan\left[\frac{1}{2} \cdot b \cdot \sqrt{2} \cdot \frac{\sqrt{a \cdot \sin(q) \cdot \cos(q) + c + i \cdot \frac{\sqrt{-a^2 \cdot \cos(q)^2 + a^2 \cdot \cos(q)^4 - c^2}}{(\sqrt{\sin(q)} \cdot \sqrt{\cos(q)})}}}{}\right]\right] \right.$$

$$\left. \sqrt{a - \frac{1}{2} \cdot \frac{\sqrt{-a^2 \cdot \cos(q)^2 + a^2 \cdot \cos(q)^4 - c^2}}{(\sin(q) \cdot \cos(q))}} \cdot \left[a \cdot \left[\left[-1 - \frac{(1-\cos(q))}{\cos(q)}\right] \cdot c\right]\right] \right| c$$

Figure 6:
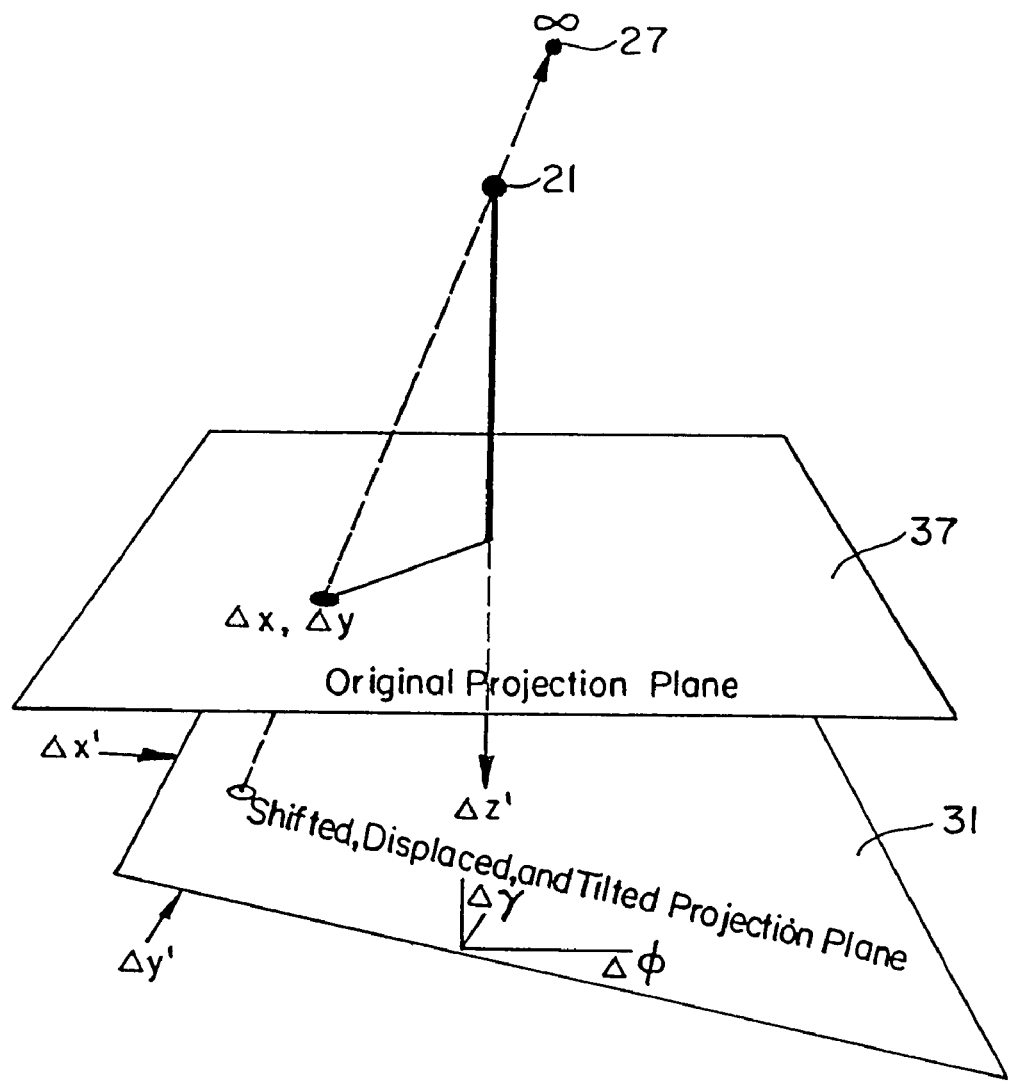
FIG. 6 is a schematic representation of a system having seven degrees of freedom in which an infinite point source is shifted relative to an original projection plane and in which a projection plane of a recording medium is shifted, displaced, and tilted relative to the original projection plane.

In FIG. 6, another arrangement of the system of the present invention is depicted wherein the radiation source 27 is located at a fixed distance from the selected object 21 and sufficiently far so that magnification is not significant. However, the recording medium 31 is allowed to be shifted, displaced, and tilted relative to the selected object 21 and an original or desired projection plane 37. In this arrangement, there are seven degrees of freedom (two translational degrees of freedom for the radiation source 27 and 2 translational, 1 displacement, and 2 tilting degrees of freedom for the recording medium 31). Therefore, a fiducial reference having at least seven degrees of freedom is needed to solve the system. Accordingly, a fiducial reference comprising at least four point-size reference markers can be used to determine the position of the radiation source relative to the selected object 21 and the recording medium 31.

Figure 7:
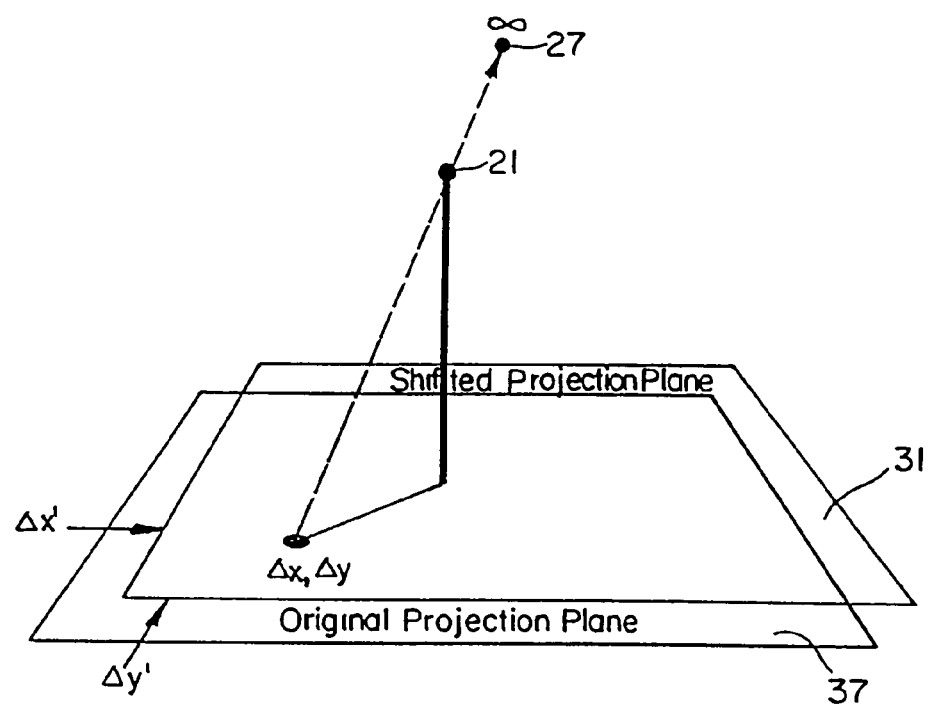
FIG. 7 is a schematic representation of a system having four degrees of freedom in which an infinite point source is shifted relative to an original projection plane and in which a projection plane of a recording medium is shifted relative to the original projection plane.

In FIG. 7, yet another arrangement of the system of the present invention is depicted wherein the distance between the object 21 and the radiation source 27 is sufficiently large so that magnification can be ignored and wherein the recording medium 31 is free to shift laterally relative to the object 21 and the desired or original projection plane 37. In this arrangement, there are four degrees of freedom (two translational degrees of freedom for the radiation source 27 and two translational degrees of freedom for the recording medium 31). Therefore, a fiducial reference having at least four degrees of freedom is necessary to completely determine the system. Accordingly, a fiducial reference comprising at least two point-size reference markers can be used to determine the position of the radiation source relative to the selected object 21 and the recording medium 31. This relatively constrained system may be useful in three-dimensional reconstructions of transmission electron micrographs produced from video projections subtending various degrees of specimen tilt and exhibiting various amounts of arbitrary and unpredictable lateral shift due to intrinsic instability associated with the instrument's electron lenses.

Referring to FIG. 1, the radiation source 27 may be either a portable or a stationary X-ray source. However, the radiation source 27 is not limited to an X-ray source. The specific type of source 27 which is utilized will depend upon the particular application. For example, the present invention can also be practiced using magnetic resonance imaging (MRI), ultrasound, visible light, infrared light, ultraviolet light, or microwaves.

Figure 10:
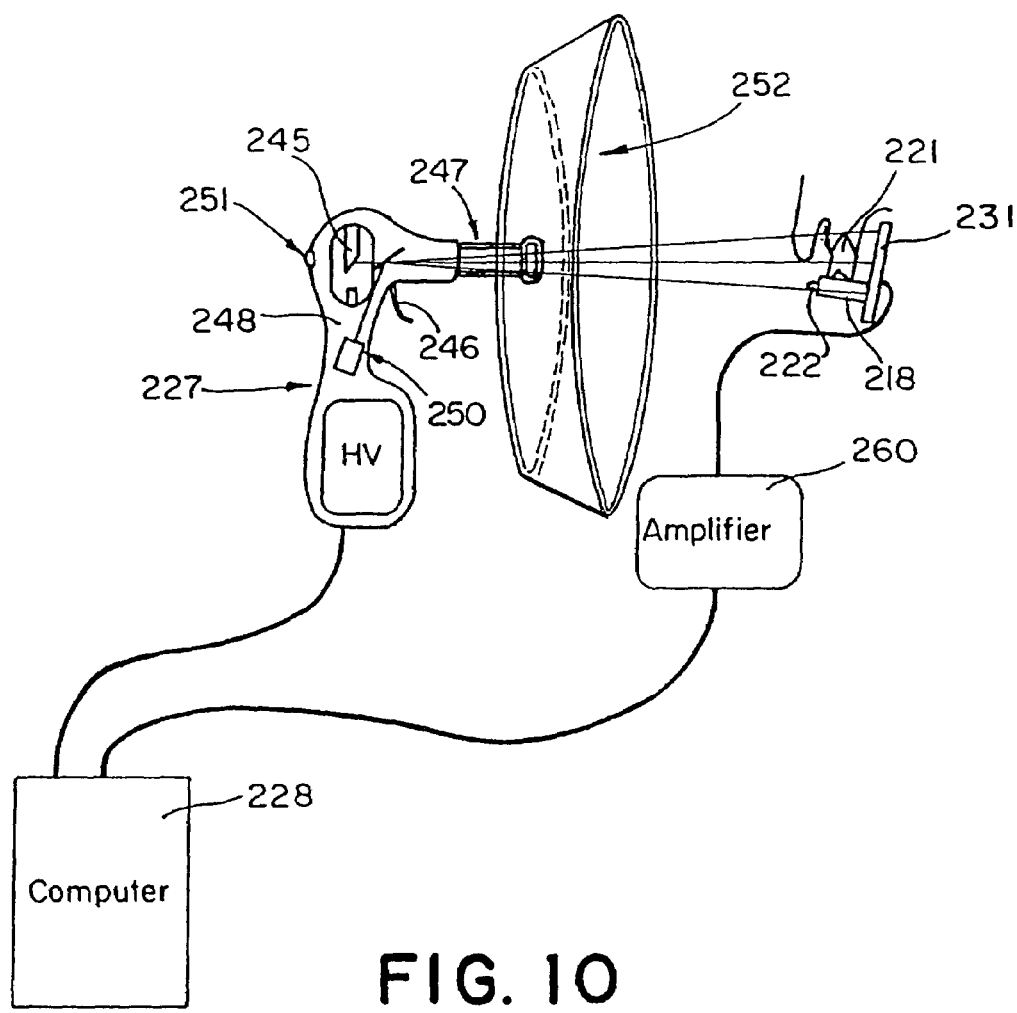
FIG. 10 is a schematic representation of an embodiment of the present invention wherein the source is a hand-held X-ray source with a laser aiming device.

In the embodiment shown in FIG. 10, the source 227 is a hand-held X-ray source, similar to that described above in reference to source 127, except that a low power laser aiming device 250 and an alignment indicator 251 are provided to insure that the source 227 and the recording medium 231 are properly aligned. In addition, a radiolucent bite block 218 is provided to constrain the detector 231 relative to the object 221, thereby constraining the system to three degrees of freedom (two translational and one displacement for the radiation source 227 relative to the object 221 and detector 231). Consequently, the fiducial reference 222 can be fixed directly to the bite block 218. When the source 227 is properly aligned with the recording medium 231, radiation emanating from the aiming device 250 impinges on the recording medium 231. In response to a measured amount of radiation impinging on the recording medium 231, a signal is sent to activate the alignment indicator 251 which preferably produces a visible and/or auditory signal. With the alignment indicator 251 activated, the X-ray source 245 can be operated at full power to record a projected image. In addition, the source 227 can optionally comprise a collimator 247 to collimate the radiation from the X-ray source and/or a transparent scatter shield 252 to protect the operator from scattered radiation. In lieu of the scatter shield 252, the operator can stand behind a radiopaque safety screen when exposing the patient to radiation from the source 227. A handle 248 and trigger 246 may be provided to facilitate the handling and operation of the source 227. The source 227 is connected to a computer/high voltage source 228 and an amplifier 260 for controlling operation of the device.

In one embodiment, the aiming device 250 comprises an X-ray source operated in an ultra-low exposure mode and the projected image is obtained using the same X-ray source operated in a full-exposure mode. Alternatively, a real-time ultra-low dose fluoroscopic video display can be mounted into the handle 248 of the source 227 via a microchannel plate (MCP) coupled to a CCD. The video display switches to a lower gain (high signal-to-noise) frame grabbing mode when the alignment is considered optimal and the trigger 246 is squeezed more tightly.

Figure 22:
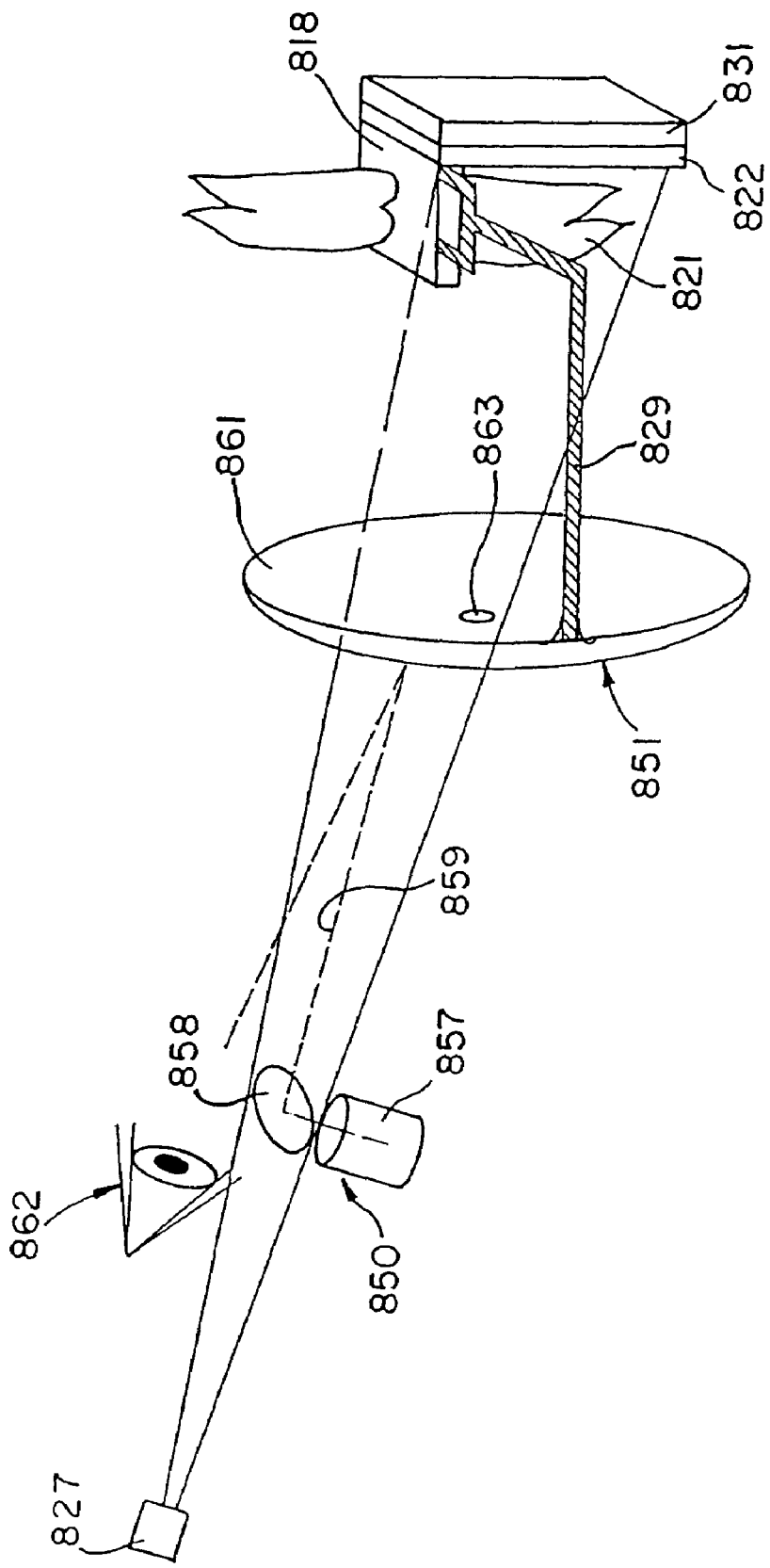
FIG. 22 is an alternate embodiment of a laser aiming device in accordance with the present invention.

An alternate embodiment of an aiming device in accordance with the present invention is shown in FIG. 22. The aiming device 850 comprises a laser source 857 and a radiolucent angled mirror 858 which produces a laser beam, illustrated by dashed line 859, which is concentric with the radiation emanating from the source 827. The alignment indicator 851 comprises a radiolucent spherical surface 861 which is rigidly positioned relative to the detector 831 by a C-arm 829 that is plugged into the bite block 818. When the aiming device 850 is aimed such that the laser beam 859 impinges upon the spherical surface 861, the specular component of the laser beam 859 is reflected by the spherical surface 861. Accordingly, proper alignment of the source 827, the object 821, and the detector 831 is obtained when the reflected portion of the laser beam 859 is within a small solid angle determined by the position of the aiming device 850. Direct observation of the reflected portion of the laser beam 859 by a detector or observer 862 can be used to verify the alignment. As shown in the figure, the fiducial reference 822 comprises a radiolucent spacer containing a fiducial pattern that is affixed to the detector 831. Further, a central ring area 863 can be designated at the center of the spherical surface 861 such that aiming the laser beam 859 at the central ring area 863 assures an essentially orthogonal arrangement of the source 827 and the detector 831. In addition, replacing the concentric laser source 857 with a laser source that produces two laser beams that are angled relative to the radiation emanating from the source 827 permits the distance between the source 827 and the detector 831 to be set to a desired distance, provided that the two laser beams are constrained to converge at the spherical surface 861 when the desired distance has been established.

Referring again to FIG. 1, the recording medium 31 is provided for recording the projected object image 40 of the selected object 21 and the projected reference images, 39 and 139, of the reference markers 23 and 123. The recording medium 31 may be in the form of a photographic plate or a radiation-sensitive, solid-state image detector such as a radiolucent charge-coupled device (CCD).

Figure 8:
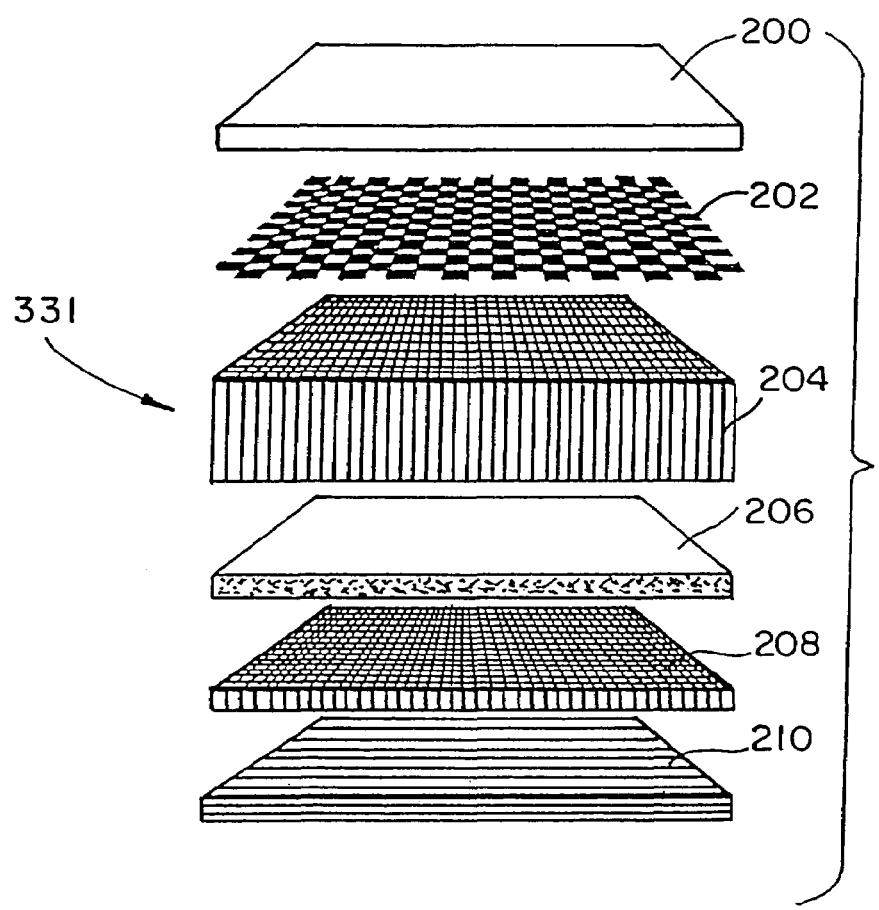
FIG. 8 is an exploded, schematic representation of a charge-coupled device (CCD) for use as a recording medium.

In one particular embodiment depicted in FIG. 8, the recording medium 331 comprises a CCD having a top screen 200, a bottom screen 206 positioned below the top screen 200, and a detector 210 positioned below the bottom screen 206. The top screen 200 is monochromatic so that a projected image projected onto the top screen 200 causes the top screen 200 to fluoresce or phosphoresce a single color. In contrast, the bottom screen 206 is dichromatic, so that the bottom screen 206 fluoresces or phosphoresces in a first color in response to a projected image projected directly onto the bottom screen 206 and fluoresces or phosphoresces in a second color in response to fluorescence or phosphorescence from the top screen 200. The detector 210 is also dichromatic so as to allow for the detection and differentiation of the first and the second colors. The recording medium 331 may also comprise a radiolucent optical mask 202 to modulate the texture and contrast of the fluorescence or phosphorescence from the top screen 200, a radiolucent fiber-optic spacer 204 to establish a known projection disparity, and a radiopaque fiber-optic faceplate 208 to protect the detector 210 from radiation emanating directly from the radiation source.

Figure 20:
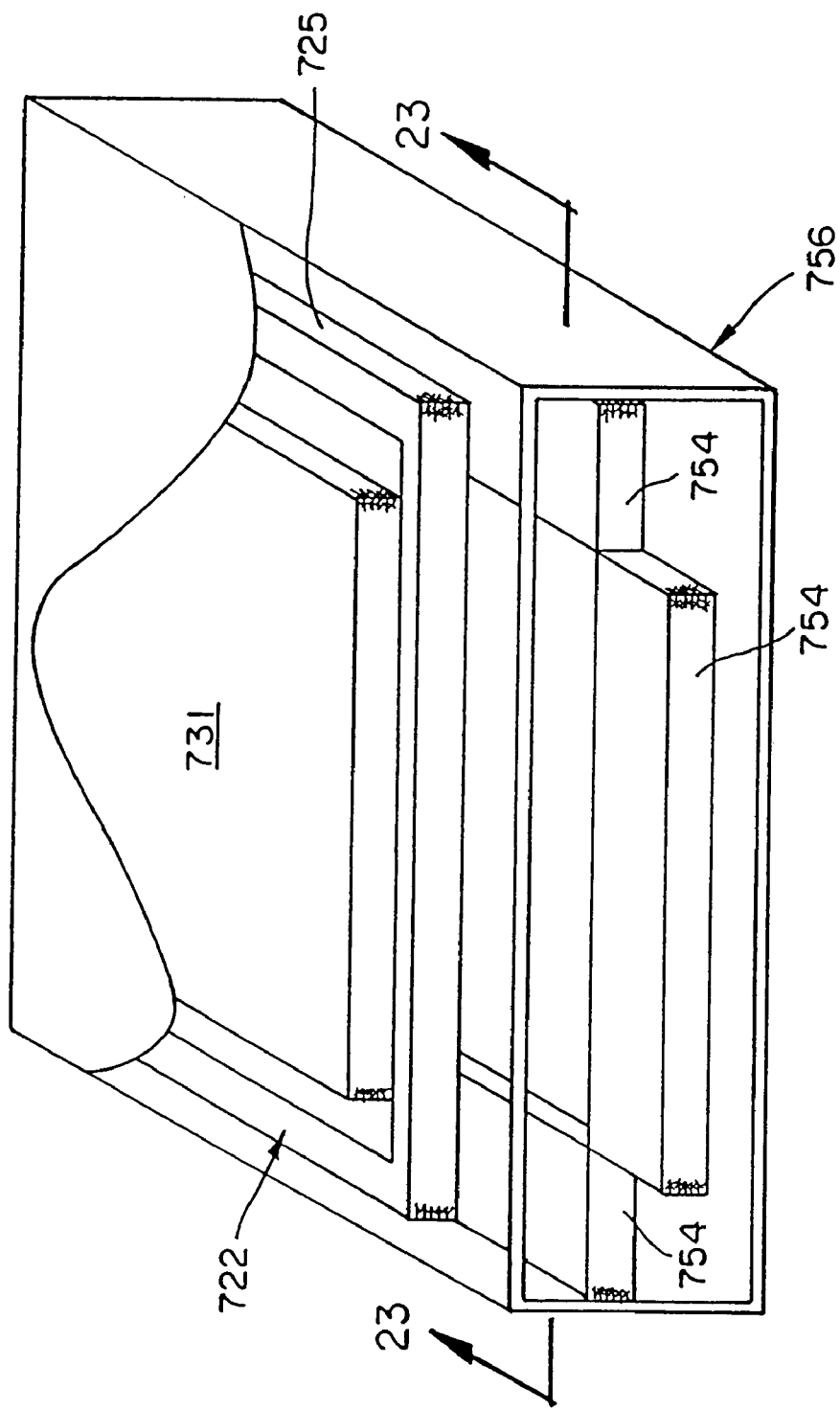
FIG. 20 is a schematic, perspective view of an embodiment of the present invention, wherein the detector comprises a charge-coupled device (CCD) and the fiducial reference comprises a frame, shown with the front and a section of the top removed.
Figure 21:
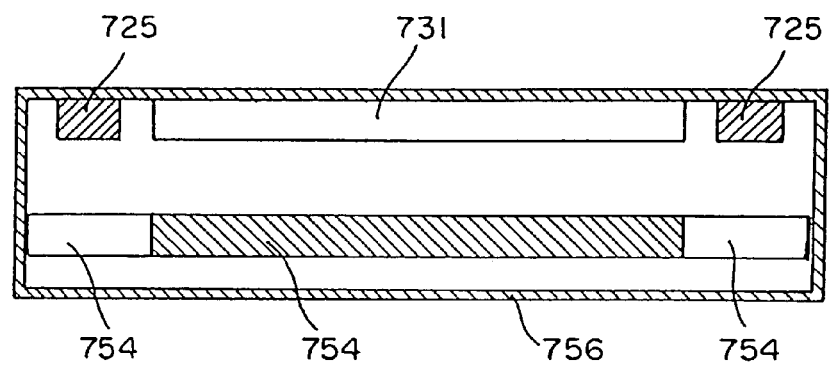
FIG. 21 is a sectional view of the embodiment depicted in FIG. 22 taken along the 23—23 line.

Yet another embodiment is depicted in FIGS. 20 and 23, wherein the detector 731 comprises a phosphor-coated CCD and the fiducial reference 722 comprises a radiopaque rectangular frame 725. Both the detector 731 and the fiducial reference 722 are contained within a light-tight package 756. The detector 731 and fiducial reference 722 are preferably positioned flush with an upper, inner surface of the package 756. The dimensions of the frame 725 are selected such that the frame 725 extends beyond the perimeter of the detector 731. Phosphor-coated strip CCDs 754 are also contained within the package 756. The strip CCDs 754 are positioned below the frame 725 such that radiation impinging upon the frame 725 castes an image of each edge of the frame 725 onto one of the strip CCDs 754. The positions of the frame shadow on the strip CCDs 754 is used to determine the projection geometry.

Figure 9:
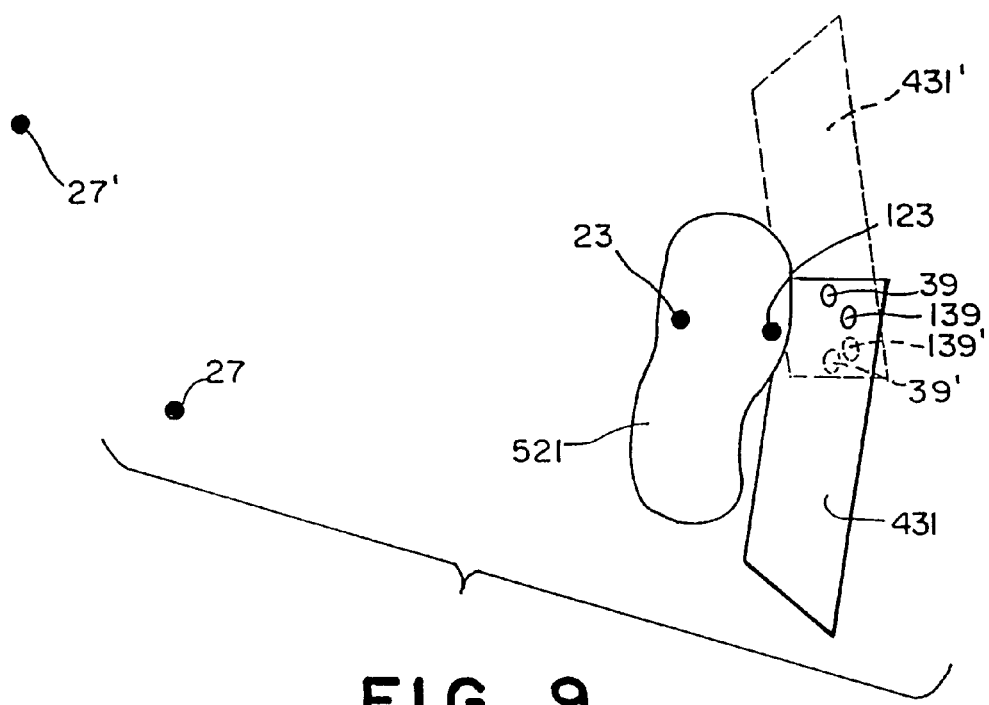
FIG. 9 is a schematic representation of an embodiment of the present invention wherein the recording medium is smaller than the projected image of the object.

In the embodiment shown in FIG. 9, the recording medium 431 is smaller than the projected image of object 521. Provided that the reference images, 39 and 139, corresponding to the reference markers, 23 and 123, can be identified on all the projected images, image slices extending across the union of all the projected images can be obtained. This is illustrated schematically in FIG. 9, wherein the reference images, 39 and 139, are taken with the source 27 and the recording medium 431 in the image positions indicated by the solid lines. Similarly, the dashed images, 39' and 139', are taken with the source 27' and the recording medium 431' in the positions indicated by the dashed lines. Accordingly, image slices of an object which casts an object image that is larger than the recording medium 431 can be synthesized. Further, by using multiple fiducial references spaced in a known pattern which are all linked to the object of interest, additional regions of commonality can be identified between multiple overlapping projection geometries, so that a region of any size can be propagated into a single, unified reconstruction. Thus, it is possible to accommodate an object much larger than the recording medium used to record individual projection images.

Figure 2:
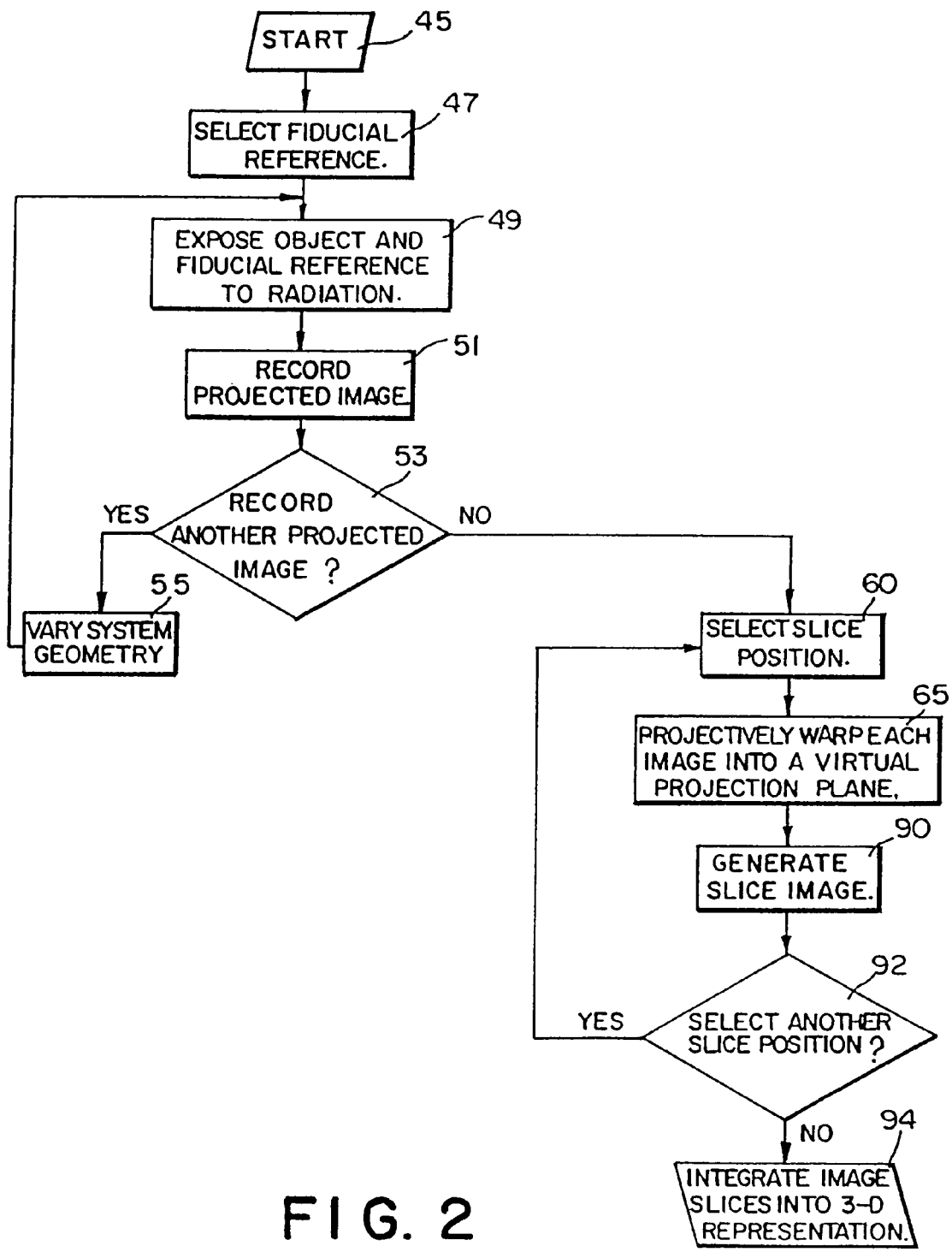
FIG. 2 is a flow chart showing the steps involved in creating three-dimensional radiographic displays using computed tomography in accordance with the present invention.

The present invention also relates to a method for creating a slice image through the object 21 of FIG. 1 from a series of two-dimensional projected images of the object 21, as shown in FIG. 2. The method of synthesizing the image slice starts at step 45. Each step of the method can be performed as part of a computer-executed process.

At step 47, a fiducial reference 22 comprising at least two reference markers, 23 and 123, is selected which bears a fixed relationship to the selected object 21. Accordingly, the fiducial reference 22 may be affixed directly to the selected object 21. The minimum required number of reference markers 23 is determined by the number of degrees of freedom in the system, as discussed above. When the fiducial reference 22 comprises reference markers 23 of a finite size, the size and shape of the reference markers 23 are typically recorded.

The selected object 21 and fiducial reference 22 are exposed to radiation from any desired projection geometry at step 49 and a two-dimensional projected image 38 is recorded at step 51. Referring to FIG. 1, the projected image 38 contains an object image 40 of the selected object 21 and a reference image, 39 and 139, respectively, for each of the reference markers 23 and 123 of the fiducial reference 22.

At step 53, it is determined whether additional projected images 38 are desired. The desired number of projected images 38 is determined by the task to be accomplished. Fewer images reduce the signal-to-noise ratio of the reconstructions and increase the intensities of component "blur" artifacts. Additional images provide information which supplements the information contained in the prior images, thereby improving the accuracy of the three-dimensional radiographic display. If additional projected images 38 are not desired, then the process continues at step 60.

If additional projected images 38 are desired, the system geometry is altered at step 55 by varying the relative positions of (1) the radiation source 27, (2) the selected object 21 and the fiducial reference 22, and (3) the recording medium 31. The geometry of the system can be varied by moving the radiation source 27 and/or the recording medium 31. Alternatively, the source 27 and recording medium 31, the selected object 21 and fiducial reference 22 are moved. When the radiation source and recording medium produce images using visible light (e.g., video camera), the geometry of the system must be varied to produce images from various sides of the object in order to obtain information about the entire object. After the system geometry has been varied, the process returns to step 49.

After all of the desired projected images have been recorded, a slice position is selected at step 60. The slice position corresponds to the position at which the image slice is to be generated through the object.

Figure 3:
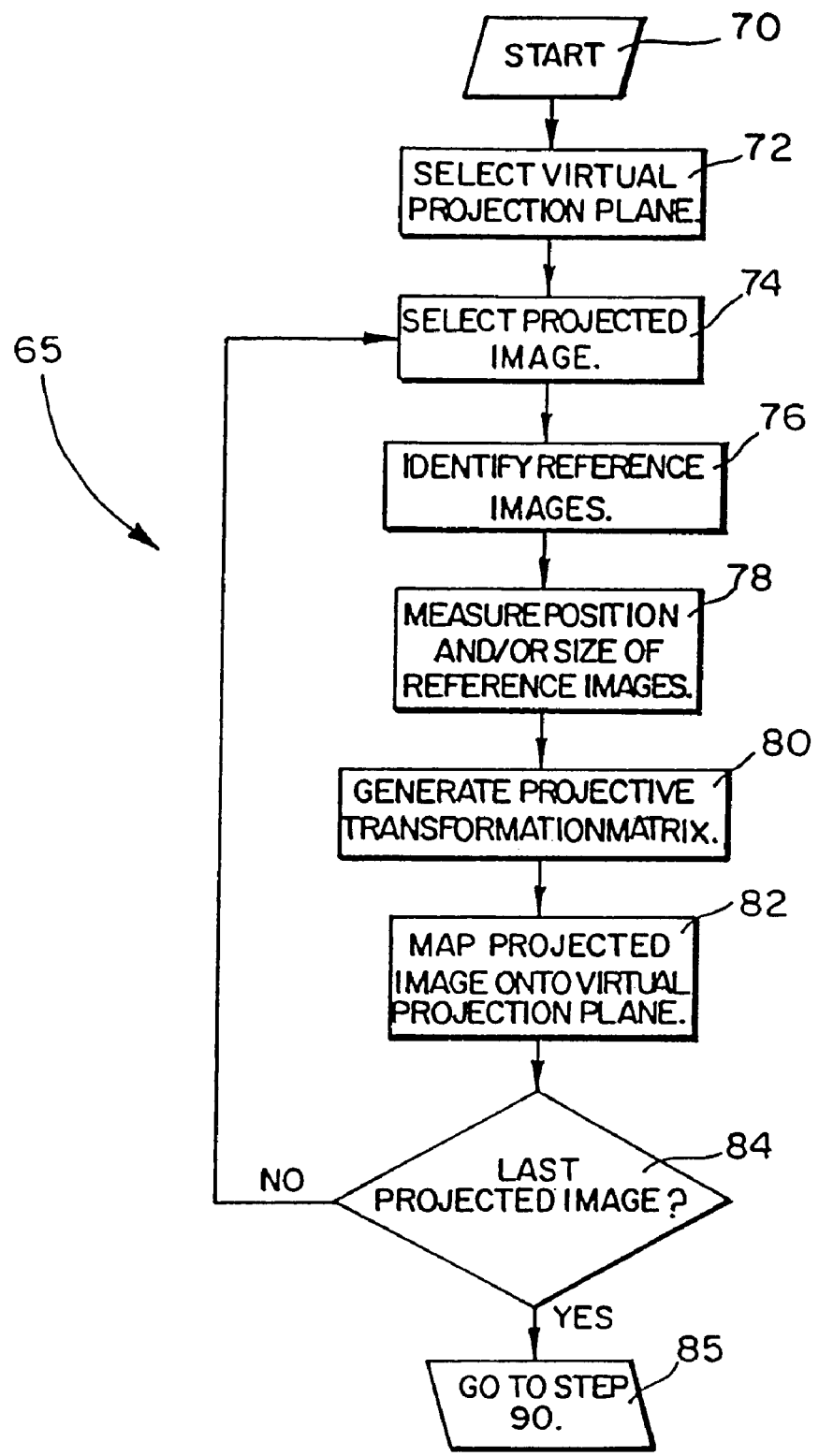
FIG. 3 is a flow chart showing details of a method of projectively warping or transforming a projected image from an actual plane of projection onto a virtual projection plane.

After the slice position has been selected, each projected image 38 is projectively warped onto a virtual projection plane 37 at step 65. The warping procedure produces a virtual image corresponding to each of the actual projected images. Each virtual image is identical to the image which would have been produced had the projection plane been positioned at the virtual projection plane with the projection geometry for the radiation source 27, the selected object 21, and the fiducial reference 22 of the corresponding actual projected image. The details of the steps involved in warping the projection plane 37 are shown in FIG. 3. The process starts at step 70.

At step 72, a virtual projection plane 37 is selected. In most cases it is possible to arrange for one of the projected images to closely approximate the virtual projection plane position. That image can then be used as the basis for transformation of all the other images 38. Alternatively, as shown for example in FIG. 4, if the fiducial reference 22 comprises more than two co-planar reference markers 23, a plane which is parallel to the plane containing the co-planar reference markers 23 can be selected as the virtual projection plane 37. When the virtual projection plane 37 is not parallel to the plane containing the co-planar reference markers 23, although the validity of the slice reconstruction is maintained, the reconstruction yields a slice image which may be deformed due to variations in magnification. The deformation becomes more prominent when the magnification varies significantly over the range in which the reconstruction is carried out. In such cases, an additional geometric transformation to correct for differential magnification may be individually performed on each projected image 38 to correct for image deformation.

One of the recorded projected images 38 is selected at step 74 and the identity of the reference images 39 cast by each reference marker 23 is determined at step 76. In the specialized case, such as the one shown in FIG. 1, where spherical reference markers 23 of the same radius are used and the relative proximal distance of each reference marker 23 to the radiation source 27 at the time that the image 38 was recorded is known, assignment of each elliptical image 39 to a corresponding reference marker 23 can be accomplished simply by inspection. Under such conditions, the minor diameter of the elliptical image 39 is always larger the closer the reference marker 23 is to the radiation source 27. This is shown most clearly in FIG. 17 wherein the minor diameter of reference image $B_s$ corresponding to reference marker B is smaller than the minor diameter of reference image $T_s$ corresponding to reference marker T. Alternatively, when applied to radiation capable of penetrating the fiducial reference 22 (i.e., X-rays), spherical reference markers 23 which are hollow having different wall thicknesses and hence, different attenuations can be used. Accordingly, the reference image 39 cast by each spherical reference marker 23 can be easily identified by the pattern of the reference images 39. Analogously, spherical reference markers 23 of different colors could be used in a visible light mediated system.

Figure 16:
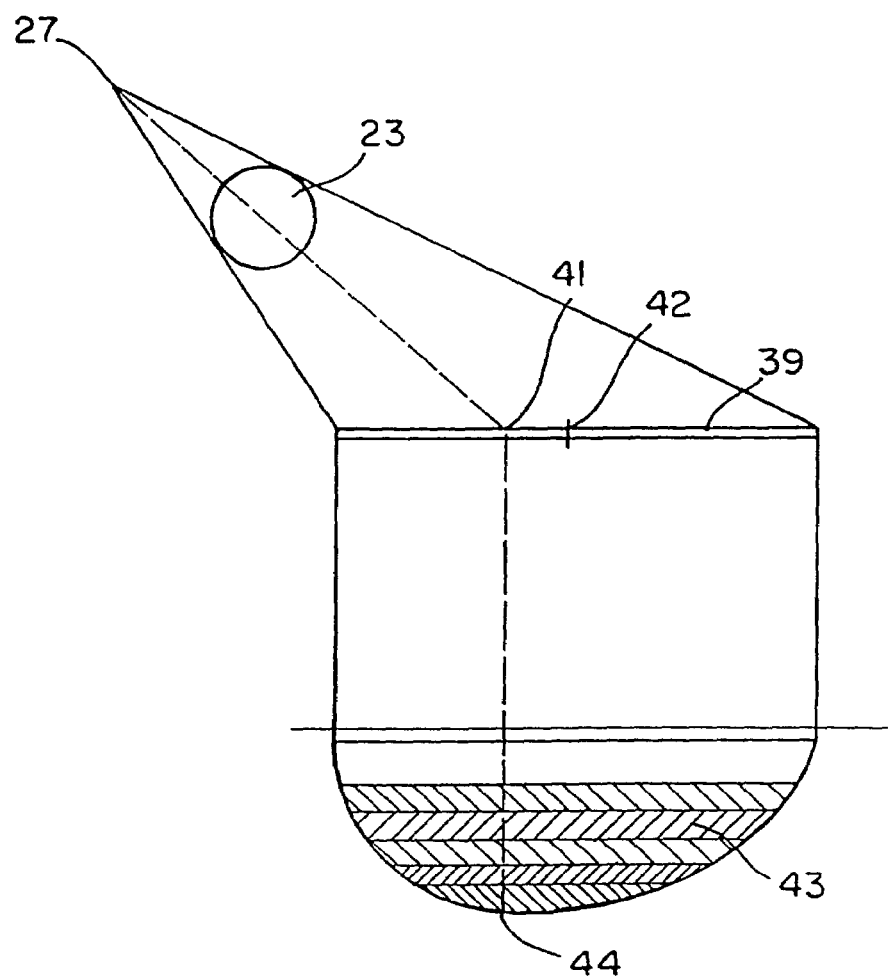
FIG. 16 is a schematic representation of a reference image cast by a spherical reference marker showing the resulting brightness profile.

The position of each reference image 39 cast by each reference marker 23 is measured at step 78. When a spherical reference marker 23 is irradiated by source 27, the projected center 41 of the reference marker 23 does not necessarily correspond to the center 42 of the reference image 39 cast by that reference marker 23. Accordingly, the projected center 41 of the reference marker 23 must be determined. One method of determining the projected center 41 of the reference marker 23 is shown in FIG. 16. The variation in intensity of the reference image 39 associated with reference marker 23 along the length of the major diameter of the reference image 39 is represented by the brightness profile 43. The method depicted in FIG. 16 relies on the fact that the projected center 41 always intersects the brightness profile 43 of the reference image 39 at, or very near, the maximum 44 of the brightness profile 43. Accordingly, the projected center 41 of a spherical reference marker 23 produced by penetrating radiation can be approximated by smoothing the reference image 39 to average out quantum mottle or other sources of brightness variations which are uncorrelated with the attenuation produced by the reference marker 23. An arbitrary point is then selected which lies within the reference image 39. A digital approximation to the projected center 41 is isolated by performing a neighborhood search of adjacent pixels and propagating the index position iteratively to the brightest (most attenuated) pixel in the group until a local maximum is obtained. The local maximum then represents the projected center 41 of the reference marker 23.

Returning to step 78 of FIG. 3, when the fiducial reference 22 comprises reference markers 23 of finite size, the sizes of each image 39 cast by each reference marker 23 are also recorded. For example, the lengths of the major and minor diameters of elliptical reference images cast by spherical reference markers 23 can be measured. Computerized fitting procedures can be used to assist in measuring the elliptical reference images 39 cast by spherical reference markers 23. Such procedures, which are well-known in the art, may be used to isolate the elliptical reference images 39 from the projected image 38 and determine the major and minor diameters of the reference images 39.

Because the attenuation of a spherical reference marker 23 to X-rays approaches zero at tangential extremes, the projected minor diameter of resulting elliptical reference images 39 will be slightly smaller than that determined geometrically by projection of the reference marker's actual diameter. The amount of the resulting error is a function of the energy of the X-ray beam and the spectral sensitivity of the recording medium 31. This error can be eliminated by computing an effective radiographic diameter of the reference marker 23 as determined by the X-ray beam energy and the recording medium sensitivity in lieu of the actual diameter.

One method of obtaining the effective radiographic diameter is to generate a series of tomosynthetic slices through the center of the reference marker 23 using a range of values for the reference marker diameter decreasing systematically from the actual value and noting when the gradient of the reference image 39 along the minor diameter is a maximum. The value for the reference marker diameter resulting in the maximum gradient is the desired effective radiographic diameter to be used for computing magnification.

Further, each projected image can be scaled by an appropriate magnification. For fiducial references 22 comprising spherical reference markers 23, the minor diameter of the reference image 39 is preferably used to determine the magnification since the minor diameter does not depend on the angle between the source 27 and the recording medium 31. Accordingly, the magnification of a spherical reference marker 23 can be determined from the measured radius of the reference marker 23, the minor diameter of the reference image 39 on the recording medium 31, the vertical distance between the center of the reference marker 23 and the recording medium 31, and the vertical distance between the recording medium 31 and the virtual projection plane 37.

Returning to FIG. 3 with reference to FIG. 1, a projection transformation matrix, representing a series of transformation operations necessary to map the selected projected image 38 onto the virtual projection plane 37, is generated at step 80. The projection transformation matrix is generated by solving each projected image 38 relative to the virtual projection plane 37. In one embodiment, the positions of the co-planar reference markers 23 are used to determine the transformation matrix by mapping the position of the reference images 39 cast by each co-planar reference marker 23 in the projected image onto its corresponding position in the virtual projection plane. For example, when the fiducial reference comprises a radiopaque frame 25, the positions of the reference images 39 cast by the reference markers 23 formed at the corners of the frame 25 are mapped to a canonical rectangle having the same dimensions and scale as the frame 25. This approach also serves to normalize the projective data. Depending on the number of degrees of freedom, the transformation operations range from complex three-dimensional transformations to simple planar rotations or translations. Once the projective transformation matrix has been generated, the matrix is used to map the projected image 38 onto the virtual projection plane 37 at step 82.

At step 84, it is determined whether all of the projected images 38 have been analyzed. If all of the projected images 38 have not been analyzed, the process returns to step 74, wherein an unanalyzed image 38 is selected. If no additional projected images 38 are to be analyzed, then the process proceeds through step 85 of FIG. 3 to step 90 of FIG. 2.

After each image has been warped onto the virtual projection plane, an image slice through the object 21 at the selected slice position is generated at step 90. An algorithm, such as that described in U.S. Pat. No. 5,359,637, which is incorporated herein by reference, can be used for that purpose. The position of the reference image cast by the alignment marker or markers 23 in each projected image 38 are used as the basis for application of the algorithm to generate the image slices.

By generating image slices at more than one slice position, a true three-dimensional representation can be synthesized. Accordingly, it is determined whether an additional slice position is to be selected at step 92. If an additional slice position is not desired, the process proceeds to step 94. If a new slice position is to be selected, the process returns to step 60.

If image slices at multiple slice positions have been generated, the entire set of image slices is integrated into a single three-dimensional representation at step 94. Alternative bases for interactively analyzing and displaying the three-dimensional data can be employed using any number of well-established three-dimensional recording and displaying methods.

In the embodiment shown in FIG. 19, the source 627 is an unconstrained point source and the detector 631 is completely constrained relative to the object 621. Accordingly, the system has three degrees of freedom (two translational and one displacement for the radiation source 627 relative to the object 621 and detector 631). A beam collimator 647 can be positioned between the source 627 and the object 621 to collimate the radiation from the source 627. The detector 631 comprises a primary imager 632 and a secondary imager 634 positioned a known distance below the primary imager 632. In one embodiment, both the primary and secondary imagers, 632 and 634, are CCD detectors. The fiducial reference 622 comprises a radiopaque shield 633 with a ring-shaped aperture 636 of known size positioned between the primary imager 632 and the secondary imager 634.

Radiation from the source 627 passes through collimator 647, irradiates object 621, and produces an object image on the primary imager 632. In addition, radiation from the source 627 which impinges upon the radiopaque shield 633 passes through the aperture 636 to produce a circular, or elliptical, reference image of the aperture 636 on the secondary imager 634. Since the secondary imager 634 is not used to record object images, the secondary imager 634 can be a low quality imager such as a low resolution CCD. Alternatively, a lower surface of the primary imager 632 can be coated with a phosphorescent material 635, so that radiation impinging upon the primary imager 632 causes the phosphorescent material 635 to phosphoresce. The phosphorescence passes through the aperture 636 to produce the reference image on the secondary imager 634.

In operation, the reference image produced using the system depicted in FIG. 19 can be used to determine the position of the source 627 relative to the object 621 and the detector 631. A circle, or ellipse, is fitted to the projected reference image. By fitting a circle, or ellipse, to the reference image, the effect of dead areas and/or poor resolution of the secondary imager 634 can be eliminated by averaging. The position of the center of the fitted circle, or ellipse, relative to the known center of the aperture 636 is determined. The angle $\alpha$ of a central ray 637 radiating from the source 627 relative to the object 621 and the detector 631 can then be determined. In addition, the length of the minor diameter of the projected reference image is determined and compared to the known diameter of the aperture 636 to provide a relative magnification factor. The relative magnification factor can then be used to determine the distance of the source 627 from the object 621.

The center of the fitted circle can be determined as follows. A pixel or point on the secondary imager 634 that lies within the fitted circle is selected as a seed point. For convenience, the center pixel of the secondary imager 634 can be selected, since the center point will typically lie within the fitted circle. A point R is determined by propagating from the seed point towards the right until the fitted circle is intersected. Similarly, a point L is determined by propagating from the seed point towards the left until the fitted circle is intersected. For each pixel along the arc L-R, the average of the number of pixels traversed by propagating from that pixel upwardly until the fitted circle is intersected and the number of pixels traversed by propagating from that pixel downwardly until the fitted circle is intersected is determined. Any statistical outliers from the averages can be discarded and the average of the remaining values calculated. This average represents the row address of the fitted circle's center. To obtain the column address, the entire reference image is rotated by 90° and the process is repeated. The row address and column address together represent the position of the center of the fitted circle.

Although the above embodiments have been described in relation to projected images of objects produced using X-rays, the present invention is equally applicable to images produced using a variety of technologies, such as visible light, ultrasound, or electron microscopy images. Specifically, intermediate voltage electron microscope (IVEM) images can be used to provide quantitative three-dimensional ultrastructural information. Further, the present invention can also be used to reconstruct three-dimensional images of objects which either emit or scatter radiation.

When IVEM images are used, the present invention allows cellular changes to be detected and quantified in an efficient and cost-effective manner. Quantitation of three-dimensional structure facilitates comparison with other quantitative techniques, such as biochemical analysis. For example, increases in the Golgi apparatus in cells accumulating abnormal amounts of cholesterol can be measured and correlated with biochemically measured increases in cellular cholesterol.

When photographic images are used, it is possible to create a true three-dimensional model of a diffusely illuminated fixed scene from any number of arbitrary camera positions and angles. The resulting three-dimensional image permits inverse engineering of structural sizes and shapes, and may be expressed as a series of topographic slices or as a projective model that can be manipulated interactively. This capability is particularly useful in retrofitting existing structures or quantifying three-dimensional attributes using non-invasive methods. In addition, the present invention can be applied to construct topological images of geological structures by recording images of the structure created by the sun.

It will be recognized by those skilled in the art that changes or modifications may be made to the above-described embodiments without departing from the broad inventive concepts of the invention. It should therefore be understood that this invention is not limited to the particular embodiments described herein, but is intended to include all changes and modifications that are within the scope and spirit of the invention as set forth in the claims.

What is claimed is:

1. A system for synthesizing an image slice of a selected object from multiple projected object images created by irradiating the object with a source of radiation, comprising:
   a. a fiducial reference located at a fixed position relative to the selected object to provide constraint for a number of degrees of freedom correlated to a number of degrees of freedom of the system, the fiducial reference comprising at least a first and a second identifiable reference marker disposed in a fixed position relative to one another, the first marker configured to permit alignment of the multiple images for construction of a tomosynthetic slice and the second reference marker configured to permit projective warping of a projected image from an actual projection plane to a virtual projection plane for construction of a tomosynthetic slice;
   b. a recording medium for recording at least one projected image of the fiducial reference and a region of interest of the selected object; and
   c. an image synthesizer for analyzing parameters related to positions and sizes of the images detected upon said recording medium to produce image translation data, and for reconstructing a tomographic slice from the object images and the translation data;
   wherein the fiducial reference, the source of radiation, and the recording medium are configured to be arbitrarily movable relative to one another.

2. A system according to claim 1 wherein the fiducial reference comprises at least one sphere.

3. A system according to claim 1 wherein the region of interest comprises a subvolume in which the magnification of the projected images is substantially constant.

4. A system according to claim 1 wherein the reference markers are distinguishable from each other.

5. A system according to claim 1 wherein the fiducial reference comprises at least nine degrees of freedom.

6. A system according to claim 1 wherein the fiducial reference comprises at least five identifiable reference markers in a fixed geometry relative to each other.

7. A system according to claim 6 wherein at least four of the reference markers are co-planar.

8. A system according to claim 7 wherein a maximum of any two of the four co-planar reference markers are co-linear.

9. A system according to claim 8 wherein a fifth reference marker is not co-planar with the four co-planar reference markers.

10. A system according to claim 6 wherein the markers are arranged in a pyramidal distribution.

11. A system according to claim 1 wherein the markers differ in opacity from one another.

12. A system according to claim 1 wherein the fiducial reference comprises a reference marker and a frame defining four additional reference markers.

13. A system according to claim 1 wherein the fiducial reference comprises a rectangular parallelepiped having at least six reference markers, each face of the parallelepiped comprising at least one reference marker.

14. A system according to claim 13 wherein the parallelepiped comprises at least two bars disposed at intersecting edges of the parallelepiped such that the bars provide at least one additional reference marker disposed at the intersection of the bars.

15. A system according to claim 1 wherein the recording medium includes a CCD device.

16. A system according to claim 1 wherein the source of radiation comprises at least one of an electron source, an x-ray source, a visible light source, an infrared light source, an ultraviolet light source, a microwave source, and an ultrasound source.

17. A system according to claim 1 wherein the source of radiation comprises magnetic resonance imaging.

18. A system for synthesizing an image slice of a selected object from multiple projected object images created by irradiating the object with a source of radiation, comprising:
   a. a recording medium for recording at least one projected image of a region of interest of the selected object;
   b. a fiducial reference located at a fixed position within the region of interest of the selected object, the fiducial reference providing constraint for a number of degrees of freedom correlated to a number of degrees of freedom of the system, the fiducial reference comprising at least a first and a second identifiable reference marker disposed in fixed position relative to one another; and
   c. an image synthesizer for analyzing parameters related to the images of the first marker to align the multiple projected object images and for analyzing parameters related to the second reference marker to projectively warp a projected image from an actual projection plane to a virtual projection plane to reconstruct a tomographic slice;
   wherein the fiducial reference, the source of radiation, and the recording medium are configured to be arbitrarily movable relative to one another.

19. A system according to claim 18 wherein the fiducial reference comprises at least one sphere.

20. A system according to claim 18 wherein the region of interest comprises a subvolume in which the magnification of the projected images is substantially constant.

21. A system according to claim 18 wherein the reference markers are distinguishable from each other.

22. A system according to claim 18 wherein the fiducial reference comprises at least nine degrees of freedom.

23. A system according to claim 18 wherein the fiducial reference comprises at least five identifiable reference markers in a fixed geometry relative to each other.

24. A system according to claim 23 wherein at least four of the reference markers are co-planar.

25. A system according to claim 24 wherein a maximum of any two of the four co-planar reference markers are co-linear.

26. A system according to claim 25 wherein a fifth reference marker is not co-planar with the four co-planar reference markers.

27. A system according to claim 23 wherein the markers are arranged in a pyramidal distribution.

28. A system according to claim 18 wherein the markers differ in opacity from one another.

29. A system according to claim 18 wherein the fiducial reference comprises a reference marker and a frame defining four additional reference markers.

30. A system according to claim 18 wherein the fiducial reference comprises a rectangular parallelepiped having at least six reference markers, each face of the parallelepiped comprising at least one reference marker.

31. A system according to claim 30 wherein the parallelepiped comprises at least two bars disposed at intersecting edges of the parallelepiped such that the bars provide at least one additional reference marker disposed at the intersection of the bars.

32. A system according to claim 18 wherein the recording medium includes a CCD device.

33. A system according to claim 18 wherein the source of radiation comprises at least one of an electron source, an x-ray source, a visible light source, an infrared light source, an ultraviolet light source, a microwave source, and an ultrasound source.

34. A system according to claim 18 wherein the source of radiation comprises magnetic resonance imaging.

35. A method for synthesizing an image slice through a selected object at a selected slice position through the object from a plurality of projected images of the object comprising the steps of:
   a. providing a fiducial reference located at a fixed position relative to the selected object to provide constraint for a number of degrees of freedom correlated to a number of degrees of freedom of the system, the fiducial reference comprising at least a first and a second identifiable reference marker disposed in a fixed position relative to one another, the first marker configured to permit alignment of the multiple images and the second reference marker configured to permit projective warping of a projected image from an actual projection plane to a virtual projection plane;
   b. recording projected images of a region of interest of the selected object and the fiducial reference on a recording means at different arbitrary relative positions between (1) a source of radiation, (2) the selected object and fiducial reference, and (3) the recording means; and
   c. synthesizing an image slice of the selected object at a selected slice position through the object from the projected images.

36. A method according to claim 35 wherein the step of synthesizing an image slice comprises aligning the projected images based on parameters related to the first marker and projectively warping a projected image from an actual projection plane to a virtual projection plane using parameters related to the second reference marker.

37. A method according to claim 35 wherein the region of interest comprises a subvolume in which the magnification of the projected images is substantially constant.

38. A method according to claim 35 comprising the step of determining the magnification of the projected image of the second reference marker.

39. A method according to claim 38 wherein the image of the second reference marker comprises a minor diameter and the step of determining the magnification uses the minor diameter to determine the magnification.

40. A method according to claim 35 comprising the step of generating a projected transformation matrix.

41. A method according to claim 40 wherein the step of generating the projected transformation matrix comprises mapping the position of the second reference marker image in the projected image onto a corresponding position of the second reference marker in a virtual projection plane.

* * * * *